United States Patent [19]

Kelly

[11] 3,946,046
[45] Mar. 23, 1976

[54] RESOLUTION OF PROSTAGLANDIN INTERMEDIATES BY MEANS OF OXAZOLIDINES

[75] Inventor: Robert C. Kelly, Kalamazoo, Mich.

[73] Assignee: The Upjohn Company, Kalamazoo, Mich.

[22] Filed: Dec. 15, 1972

[21] Appl. No.: 315,726

Related U.S. Application Data

[60] Division of Ser. No. 181,246, Sept. 16, 1971, Pat. No. 3,711,515, which is a continuation-in-part of Ser. No. 93,483, Nov. 27, 1970, abandoned.

[52] U.S. Cl. .................................. 260/343.3 R
[51] Int. Cl.² .................................. C07D 307/83
[58] Field of Search .......................... 260/343.3

[56] References Cited
OTHER PUBLICATIONS

Corey et al., JACS, 92:2, Jan. 28, 1970, pp. 397–398.

Primary Examiner—R. J. Gallagher
Assistant Examiner—Anne Marie T. Tighe
Attorney, Agent, or Firm—Morris L. Nielsen

[57] ABSTRACT

Process for resolving a racemic mixture of an oxo-type prostaglandin intermediate by (a) converting the oxo compound by reaction with an optically active ephedrine to a mixture of oxazolidine diastereomers, (b) separating at least one oxazolidine diastereomer from said mixture, (c) hydrolyzing said oxazolidine to free the optically active oxo compound, and (d) recovering said optically active oxo compound.

11 Claims, No Drawings

RESOLUTION OF PROSTAGLANDIN INTERMEDIATES BY MEANS OF OXAZOLIDINES

CROSS REFERENCE TO RELATED APPLICATIONS

This is a division of then copending application Ser. No. 181,246 filed Sept. 16, 1971, now issued as U.S. Pat. No. 3,711,515, which was a continuation-in-part of then copending application Ser. No. 93,483, filed Nov. 27, 1970, and since abandoned.

BACKGROUND OF THE INVENTION

This invention relates to a process for preparing intermediates useful in the preparation of prostaglandins, (hereinafter identified as "$PGE_2$," "$PGF_2\alpha$," etc.) and to a process for preparing racemic and optically active $PGE_3$ and $PGF_3\alpha$, their enantiomorphs and their 15-epimers.

Previously, the preparation of a racemic bicyclic lactone diol of the formula

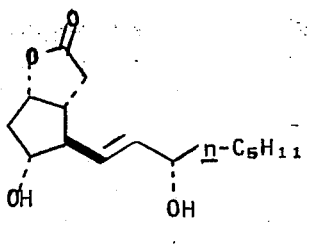

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGF_2\alpha$, either in dl-form or optically active form, was disclosed in those publications.

It is well known that the prostaglandin structures have several centers of asymmetry and therefore exist as stereoisomers (see Nugteren et al., Nature 212, 38–39 (1966); Bergstrom et al., Pharmacol. Rev. 20, 1 (1968)). Each formula for $PGE_2$, $PGF_2\alpha$, $PGE_3$, and $PGF_3\alpha$ herein represents a molecule of the optically active naturally-occuring from of the prostaglandin.

$PGE_2$ has the following structure:

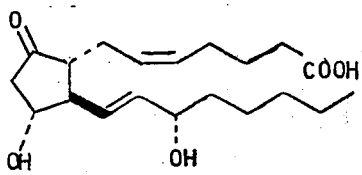

$PGF_2\alpha$ has the following structure:

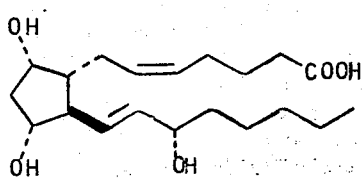

$PGE_3$ has the following structure:

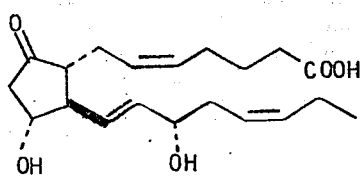

$PGF_3\alpha$ has the following structure:

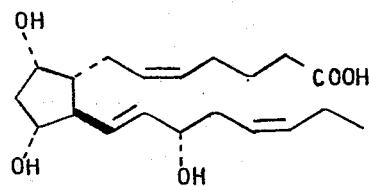

See also FIGS. XVI, XXII, XXIV, and XXVI herein, which are identical to the above formulas when ~ represents attachment of hydroxyl in the α (S) configuration. The mirror image of each formula represents a molecule of the enantiomorphic form of that prostaglandin. Thus, for example, "ent-$PGE_3$" refers to the enantiomorph of $PGE_3$. The racemic or "dl" form of the prostaglandin consists of equal numbers of two types of molecules, e.g., a natural-configuration prostaglandin and its enantiomorph. If one of the optically active isomers has dextro optical rotatory power, the other has an equal degree of laevo optical rotatory power. A racemic mixture of equal quantities of d- and l- isomers exhibits no optical rotation. The reaction of the components of a racemic mixture with an optically-active substance results in the formation of diastereomers having different physical properties, e.g. degree of solubility in a solvent. Another term used herein is "15—epimer." When referred to one of the above prostaglandins, it identifies a molecule having the opposite configuration at the C—15 atom. Thus, "15β—$PGE_3$ refers to the product having the β (R) configuration at carbon 15 as compared with the α (S) configuration for $PGE_3$.

$PGE_2$, $PGF_2\alpha$, $PGF_2\beta$, and $PGA_2$, and their esters, acylates, and pharmocologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the $PGE_2$, $PGF_2\beta$, and $PGA_2$ compounds as measured, for example, in anesthetized (pentobarbital sodium) pentolinium-treated rats with indwelling aortic and right heart cannulas; pressor activity, similarly measured, for the $PGF_2\alpha$ compounds; stimulation of smooth muscle as shown, for example, by tests on strips of guinea pig ileum, rabbit duodenum, or gerbil colon; potentiation of other smooth muscle stimulants, antilipolytic activity as shown by antagonism of epinephrine-induced mobilization of free fatty acids or inhibition of the spontaneous release of glycerol from isolated rat fat pads; inhibition of gastric secretion in the case of the $PGE_2$ and $PGA_2$ compounds as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the $PGE_2$ compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the $PGE_2$ compounds, are useful in mammls, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The $PGE_2$ and $PGA_2$ compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day are used, the exact dose depending on the age, weight, and condition of the patient or animal, and on the frequency and route of administration.

The $PGE_2$, $PGF_{2\alpha}$, and $PGF_{2\beta}$ compound are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The $PGE_2$, $PGF_{2\alpha}$, and $PGF_{2\beta}$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

$PGE_2$ compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the $PGE_2$ compound is administered by intravenous infusion immediately after abortion or delivery at a dose in the range about 0.01 to about 50 $\mu$g. per. kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The $PGE_2$, $PGF_{2\beta}$, and $PGA_2$ compounds are useful as hypotensive agents to reduce blood pressure in mammals including man. For this purpose, the compounds are administered by intravenous infusion at the rate of about 0.01 to about 50 $\mu$g. per kg. of body weight per minute, or in single or multiple doses of about 25 to 500 $\mu$g. per kg. of body weight total per day.

The $PGE_2$, $PGF_{2\alpha}$, and $PGF_{2\beta}$ compounds are useful in place of oxytocin to induce labor in pregnant female animals, including man, cows, sheep and pigs, at or near term, or in pregnant animals with intrauterine death of the fetus from about 20 weeks to term. For this purpose, the compound is infused intravenously at a dose 0.01 to 50 $\mu$g. per. kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The $PGE_2$, $PGF_{2\alpha}$, and $PGF_{2\beta}$ compounds are useful for controlling the reproductive cycle in ovulating female mammals, including humans and other animals. For that purpose, $PGF_2$, for example, is administered systemically at a dose level in the range dl-Tricyclic 20 mg. per kg. of body weight, advantageously during a span of time starting approximately at the time of ovulation and ending approximately at ~time of menses or just prior to menses. Additionally, expulsion of an embryo or a fetus is accomplished by similar administration of the compound during the first third of the normal mammalian gestation period. Because the $PGE_2$ compounds are potent antagonists of epinephrine-induced mobilization of free fatty acids, they are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The $PGE_2$ compounds promote and accelerate the growth of epidermal cells and keratin in animals, including humans, and other animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 5 to 1000 μg./ml. of the $PGE_2$ compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

SUMMARY OF THE INVENTION

It is the purpose of this invention to provide processes for the production of compounds useful in the preparation of prostaglandins commercially in substantial amount and at reasonable cost. It is a further purpose to provide processes for preparing certain intermediates in optically active forms. It is still a further purpose to provide a process for preparing racemic and optically active $PGE_3$, $PGF_{3\alpha}$, $PGF_{3\beta}$, and $PGA_3$, their enantiomorphs, and their 15-epimers.

The presently described processes and intermediates are useful for preparing $PGE_2$, $PGF_{2\alpha}$, and $PGA_2$ and their racemic forms, which are known to be useful for the above-described pharmacological purposes. The processes and intermediates disclosed herein are also useful for preparing enantiomorphic $PGE_2$, $PGF_{2\alpha}$, $PGF_{2\beta}$ and $PGA_2$, and $PGE_3$, $PGF_{3\alpha}$, $PGF_{3\beta}$, and $PGA_3$, their enantiomorphs, and their 15β-epimers, each one of which is useful for the above-described pharmacological purposes, and is used for those purposes in the same manner as described above. These novel compounds are substantially more specific with regard to potency in causing prostaglandin-like biological responses. Therefore, each of these novel prostaglandin-type compounds is surprisingly and unexpectedly more useful than one of the corresponding above-mentioned known prostaglandins for at least one of the pharmacological purposes indicated above for the latter, because it has a different and narrower spectrum of biological potency than the known prostaglandins, and therefore is more specific in its activity and causes smaller and fewer undesired side effects than when the known prostaglandin is used for the same purpose.

Thus, there is provided a process for preparing an optically active tricyclic lactone glycol of the formula

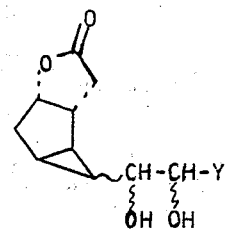

or the mirror image thereof, or a racemic compound of that formula and the mirror image thereof, wherein Y is 1-pentyl or 1-pent-2-ynyl, and ~ indicates attachment of the moiety to the cyclopropane ring in exo or endo configuration and to the side chain in alpha or beta configuration, which comprises the steps of:

a. converting optically active or racemic bicyclo[3.1.0]hex-2-ene-6-carboxaldehyde to an optically active acetal of the formula

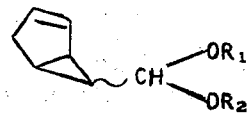

or the mirror image thereof, or a racemic compound of that formula and the mirror image thereof, wherein $R_1$ and $R_2$ are alkyl of one to 4 carbon atoms, inclusive, or, when taken together,

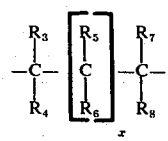

wherein $R_3$, $R_4$, $R_5$, $R_6$, $R_7$, and $R_8$ are hydrogen, alkyl of one to 4 carbon atoms, inclusive, or phenyl, with the proviso that not more than one of the R's is phenyl and the total number of carbon atoms is from 2 to 10, inclusive; $x$ is zero or one, and ~ is as defined above;

b. Transforming said optically active or racemic acetal to an optically active tricyclic mono or dihaloketone of the formula

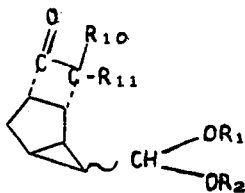

or the mirror image thereof, or a racemic compound of that formula and the mirror image thereof, wherein $R_1$, $R_2$, and $\sim$ are as defined above, and wherein $R_{10}$ is bromo or chloro, and $R_{11}$ is hydrogen, bromo, or chloro;

c. Transforming said optically active or racemic tricyclic mono or dihaloketone to an optically active tricyclic ketone of the formula

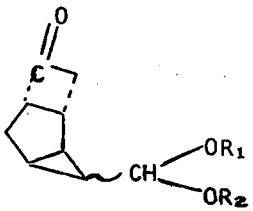

or the mirror image thereof, or a racemic compound of that formula and the mirror image thereof, wherein $R_1$, $R_2$, and $\sim$ are as defined above;

d. oxidizing said optically active or racemic tricyclic ketone to an optically active tricyclic lactone acetal of the formula

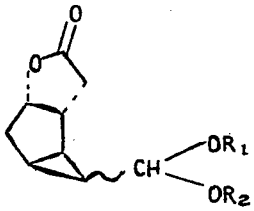

or the mirror image thereof, or a racemic compound of that formula and the mirror image thereof, wherein $R_1$, $R_2$, and $\sim$ are as defined above;

e. hydrolyzing said optically active or racemic tricyclic lactone to an optically active tricyclic lactone aldehyde of the formula

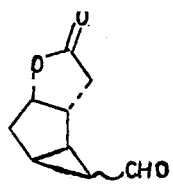

or the mirror image thereof, or a racemic compound of that formula and the mirror image thereof, wherein $\sim$ is as defined above;

f. converting said optically active or racemic tricyclic lactone aldehyde to an optically active tricyclic lactone alkene or alkenyne of the formula

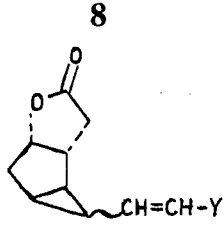

or the mirror image thereof, or a racemic compound of that formula and the mirror image thereof, wherein Y and are as defined above; and g. hydroxylating said optically active or racemic tricyclic lactone alkene or alkenyne to form said optically active or racemic tricyclic lactone glycol.

Reference to Chart A, herein, will make clear the transformation from bicyclic akdehyde 1 to tricyclic lactone glycol VIII by steps a–g, inclusive. Formulas I–X, inclusive, hereinafter referred to, are depicted in Chart A, wherein $R_1$ and $R_2$ are alkyl of one to 4 carbon atoms, inclusive, or, when taken together, $$-\underset{R_4}{\underset{|}{\overset{R_3}{\overset{|}{C}}}}-\left[\underset{R_6}{\underset{|}{\overset{R_5}{\overset{|}{C}}}}\right]_x-\underset{R_8}{\underset{|}{\overset{R_7}{\overset{|}{C}}}}-$$

wherein $R_3$, $R_4$, $R_5$, $R_6$, $R_7$, and $R_8$ are hydrogen, alkyl of one to 4 carbon atoms, inclusive, or phenyl, with the proviso that not more than one of the R's is phenyl and the total number of carbon atoms is from 2 to 10, inclusive; and $x$ is zero or one; wherein $R_9$ is alkyl of one to 5 carbon atoms, inclusive, $R_{10}$ is bromo or chloro, and $R_{11}$ is hydrogen, bromo, or chloro; wherein Y is 1-pentyl or 1-pent-2-ynyl; wherein W is 1-pentyl, cis 1-pent-2-entyl, or 1-pent-2-ynyl; and wherein $\sim$ indicates attachment of the moiety to the cyclopropane ring in exo or endo configuration, or attachment of the hydroxyl to the side chain in alpha or beta configuration.

In the formulas herein, the broken line attachments to a ring represent substituents in alpha configuration, i.e., below the plane of the paper. The wavy line $\sim$ indicates attachment of a group to a cyclopentane or lactone ring in alpha or beta configuration, or it indicates attachment to a cyclopropane ring in exo or endo configuration, or it indicates attachment to the C–15 carbon of the prostamoic acid skeleton in $\alpha$ (S) or $\beta$ (R) configuration. The formula of each intermediate as drawn herein is intended to represent the particular optical isomer which is transformed by the processes herein to an optically active prostaglandin having the natural configuration of prostaglandins obtained from mammalian tissues. The mirror image of each formula then represents a molecule of the enantiomorphic form of that intermediate. The expression "racemic compound" refers to a mixture of the optically active isomer which yields the natural configuration prostaglandin and the potically active isomer which is its enantiomorph.

CHART A

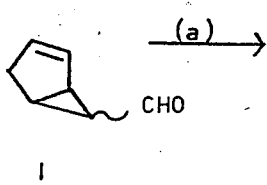

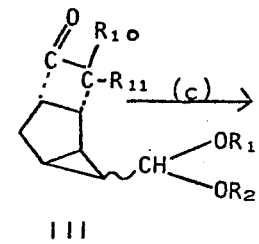

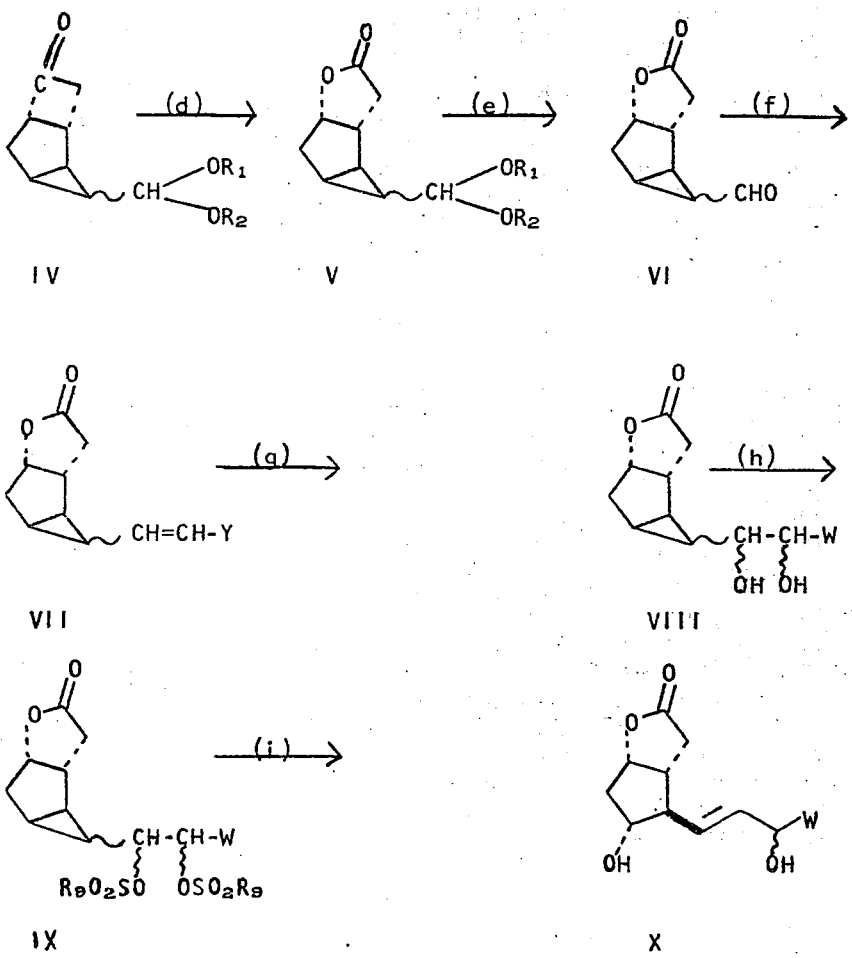

IV   V   VI

VII   VIII

IX   X

The bicyclic aldehyde of Formula I in Chart A exists in a number of isomeric forms. With respect to the attachment of the —CHO group, it exists in two isomeric forms, exo and endo. Also, with respect to the position of the cyclopentene double bond relative to the —CHO group, each of the exo and endo forms exists in two optically active (d- or l-) forms, making in all four isomers. Each of those isomers separately or mixtures thereof undergo the reactions herein for producing prostaglandin intermediates and products. For racemic products the unresolved isomers are used. For the optically active prostaglandins, the aldehyde or subsequent intermediate isomers are resolved by my new process disclosed herein, and are used for preparing the optically active products. The preparation of the exo and endo aldehydes is discussed below under "Preparations."

In carrying out step a, bicyclic aldehyde I is transformed to acetal II by methods known in the art. Thus, aldehyde I is reacted with either an alcohol of one to 4 carbon atoms, e.g., methanol, ethanol, propanol, or butanol in their isomeric forms, or mixture of such alcohols, or, preferably, a glycol having the formula VI:

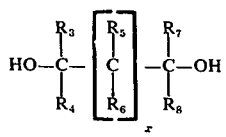

wherein $R_3$, $R_4$, $R_5$, $R_6$, $R_7$, and $R_8$ are hydrogen, alkyl of one to 4 carbon atoms, inclusive, or phenyl, with the proviso that not more than one of the R's is phenyl and the total number of carbon atoms is from 2 to 10, inclusive; and x is zero or one. Examples of suitable glycols are ethylene glycol, 1,2-propanediol, 1,2-hexanediol, 1,3-butanediol, 2,3-pentanediol, 2,4-hexanediol, 3,4-octanediol, 3,5-nonanediol, 2,2-dimethyl-1,3-propanediol, 3,3-dimethyl-2,4-heptanediol, 4-ethyl-4-methyl-3,5-heptanediol, phenyl-1,2-ethanediol, and 1-phenyl-1,2-propanediol.

The step-a reaction is carried out under a variety of conditions using procedures generally known in the art. Thus, the reactants are dissolved in benzene and the mixture heated to remove the water formed azeotropically. To accelerate the reaction, there may be added an acid catalyst such as p-toluenesulfonic acid, trichloroacetic acid, zinc chloride, and the like. Alternatively, the reactants, together with the acid catalyst and a water scavenger such as trimethyl orthoformate are warmed to 40°–100°C. in an inert solvent such as benzene, toluene, chloroform, or carbon tetrachloride. The ratio of the aldehyde to the glycol is preferably between 1:1 and 1:4.

In transforming acetal II to ketone IV, reactions known in the art for analogous compounds are employed. In carrying out step b, acetal II is reacted with a ketene $R_{10}R_{11}C=C=O$, for example $HBrC=C=O$, $HClC=C=O$, $Br_2C=C=O$, or $Cl_2C=C=O$. For convenience, ketene $Cl_2C=C=O$ is preferably. It is preferably generated in situ by the reaction of a 0.5-to-2.0-fold excess of dichloroacetyl chloride in the presence of a tertiary amine, e.g., triethylamine, tributylamine, pyridine, or 1,4-diazabicyclo[2.2.2]octane, in a solvent such as n-hexane, cyclohexane, or mixture of isomeric hexanes (Skellysolve B) at a temperature of from 0° to 70 °C. (See, for example, Corey et al., Tetrahedron Letters No. 4, pp. 307–310, 1970). Alternatively, the ketene $Cl_2C=C=O$ is generated by adding a trichloroacyl halide to zinc dust suspended in the reaction vessel, omitting the tertiary amine.

In carrying out step c, mono- or dihaloketone III is reduced with a 2-to-5-fold excess of zinc dust over the stoichiometric ratio of Zn:2Cl in methanol, ethanol, ethylene, glycol, and the like, in the presence of acetic acid, ammonium chloride, sodium bicarbonate or sodium dihydrogen phosphate. Alternatively, the reaction is carried out with aluminum amalgam in a water-containing solvent such as methanol-diethyl ether-water, tetrahydrofuran-water, or dioxane-water, at about 0°–50° C.

In carrying out step d, tricyclic acetal ketone IV is converted to a lactone by methods known in the art, for example by reaction with hydrogen peroxide, peracetic acid, perbenzoic acid, m-chloroperbenzoic acid, and the like, in the presence of a base such as alkali hydroxide, bicarbonate, or orthophosphate, using a preferred molar ratio of oxidizer to ketone of 1:1.

In carrying out step e, lactone acetal V is converted to aldehyde VI by acid hydrolysis, known in the art, using dilute mineral acids, acetic or formic acids, and the like. Solvents such as acetone, dioxane, and tetrahydrofuran are used.

In carrying out step f, aldehyde VI is transformed to the Formula-VII alkene or alkenyne, for example by means of an ylid as in the Wittig reaction. A 1-hexyl halide or 1-hex-3-ynyl halide, preferably the bromide, is used to prepare the Wittig reagent, e.g. hexyltriphenylphosphonium bromide or (hex-3-ynyl)triphenylphosphonium bromide.

In carrying out step g, the Formula-VII alkene or alkenyne is hydroxylated to glycol VIII by procedures known in the art. See South African Pat. No. 69/4809 issued July 3, 1970. In the hydroxylation of the respective endo or exo alkenes, various isomeric glycols are obtained depending on such factors as whether the —CH=CH—moiety in VII is cis or trans, and whether a cis or a trans hydroxylation reagent is used. Thus, endo-cis olefin gives a mixture of two isomeric erythro glycols of Formula VIII with a cis hydroxylation agent, e.g., osmium tetroxide. Similarly, the endotrans olefin gives a similar mixture of the same two erythro glycols with a trans hydroxylation agent, e.g., hydrogen peroxide. The endo-cis olefins and the endo-trans olefins give similar mixtures of two threo glycol isomers with trans and cis hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Chart A to produce intermediate products of Formula X and then, according to Charts C through F hereinafter to produce the other final products of this invention. Thus, the various isomeric glycol mixtures encompassed by Formula VIII produced from the various isomeric olefins encompassed by Formula VII are all useful for these same purposes.

CHART B

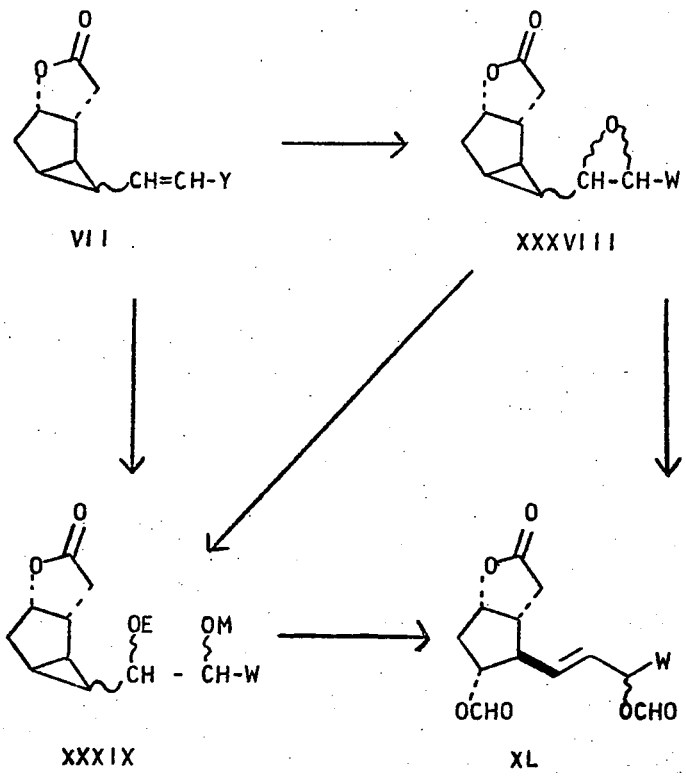

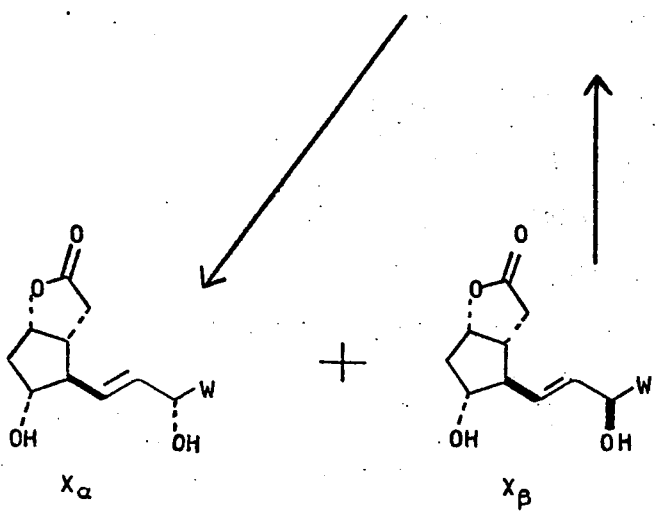
CHART C
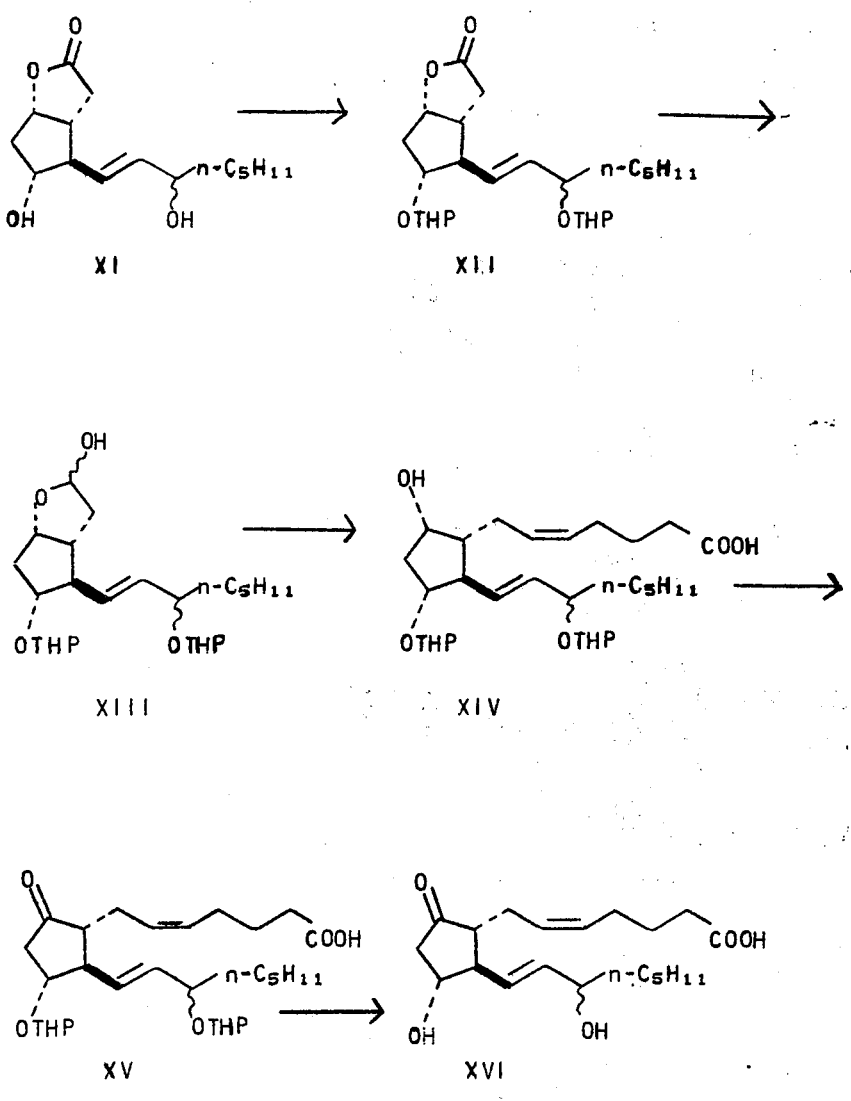

CHART D
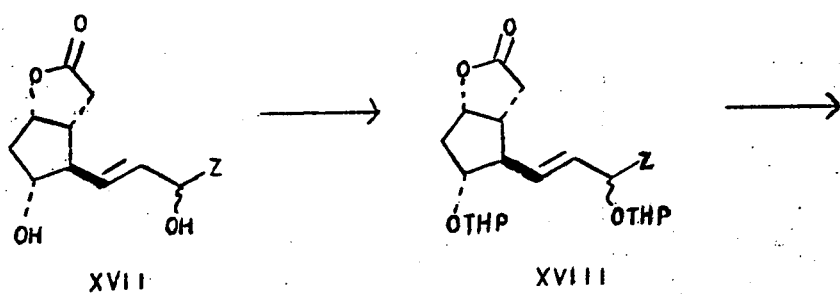
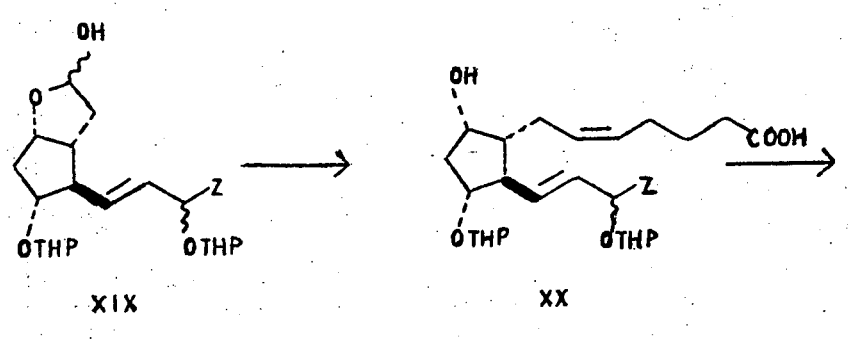
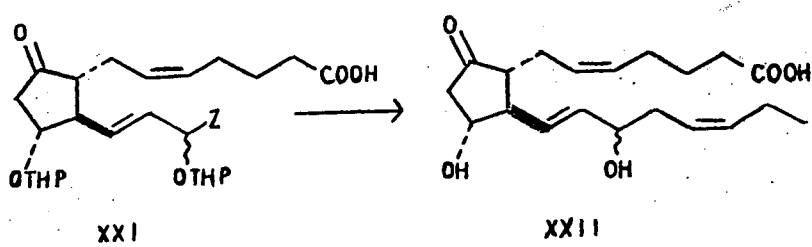
CHART E
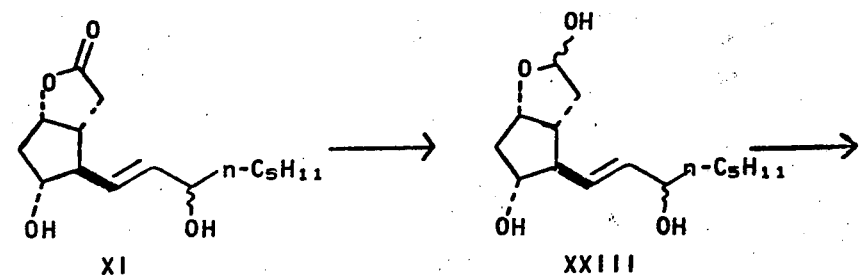
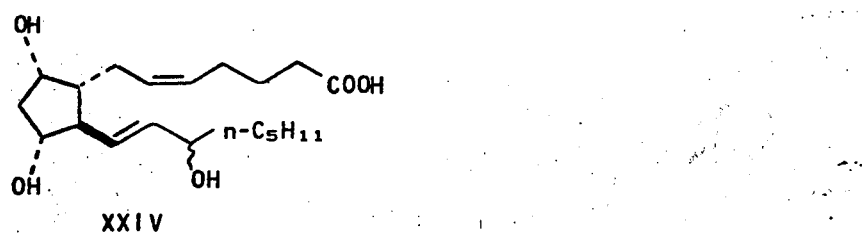

CHART F

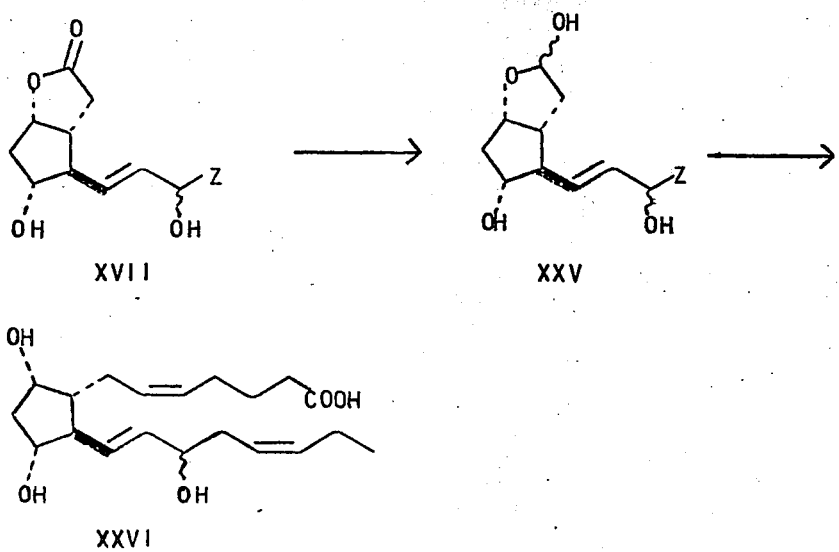

There is further provided by this invention a process for preparing an optically active bicyclic lactone diol of the formula

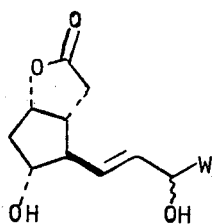

or the mirror image thereof, or a racemic compound of that formula and the mirror image thereof, wherein W is 1-pentyl, cis 1-pent-2-enyl, or 1-pent-2-ynyl, and ~ indicates attachment of the hydroxyl to the side chain in alpha or beta configuration, which comprises the steps of:

a. replacing the glycol hydrogens of an optically active tricyclic lactone glycol of the formula

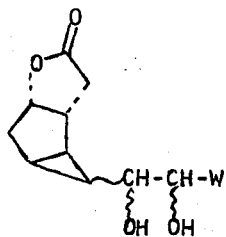

or the mirror image thereof, or a racemic compound of that formula and the mirror image thereof, by an alkanesulfonyl group, $R_9O_2S-$, wherein $R_9$ is alkyl of one to 5 carbon atoms, inclusive, and ~ indicates attachment of the moiety to the cyclopropane ring in exo or endo configuration and to the side chain in alpha or beta configuration; and b. mixing the compound formed in step a with water at a temperature in the range of 0° to 60 °C. to form said optically active or racemic bicyclic lactone diol.

Glycol VIII is transformed by steps h and i into diol X as shown in Chart A. The procedures for forming the Formula-IX bis(alkanesulfonic acid) ester by replacing the glycol hydrogen by an alkanesulfonyl group, and subsequently hydrolyzing that ester to diol X are known in the art (see South African patent cited immediately above).

In Chart A, there are differences in the terminal groups on the side chains of Formulas VII and VIII. In Formula VII, Y is limited to 1-pentyl or 1-pent-2-ynyl whereas in Formula VIII, W includes 1-pentyl, cis 1-pent-2-enyl, or 1-pent-2-ynyl. The compounds of Formula VIII, IX, or X wherein W is cis 1-pent-2-enyl are obtained by reducing the $-C \equiv C-$ moiety of the 1-pent-2-ynyl group to cis $-CH=CH-$ before or after any of the steps h or i, i.e., at any stage after the hydroxylation of the $-CH=CH-$ moiety in step g. For that purpose, there are used any of the known reducing agents which reduce an acetylenic linkage to a cis-ethylenic linkage. Especially preferred for that purpose are diimide or hydrogen and a catalyst, for example, palladium (5%) on barium sulfate, especially in the presence of pyridine. See Fieser et al., "Reagents for Organic Synthesis," pp. 566–567, John Wiley & Sons, Inc., New York, N.Y. (1967).

There is further provided a process for preparing an optically active bicyclic lactone diol of the formula

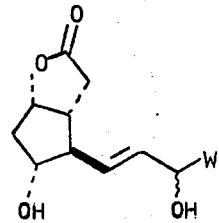

or the mirror image thereof, or a racemic compound of that formula and the mirror image thereof, wherein W is 1-pentyl, cis 1-pent-2-enyl, or 1-pent-2-ynyl, and ~ indicates attachment of the hydroxyl to the side chain in alpha or beta configuration, which comprises starting with an optically active tricyclic lactone alkene or alkenyne of the formula

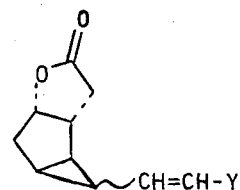

or the mirror image thereof, or a racemic compound of that formula and the mirror image thereof, wherein Y is 1-pentyl or 1-pent-2-ynyl and ~ indicates attachment of the moiety to the cyclopropane ring in exo or endo configuration, and subjecting said alkene or alkenyne successively to the following reactions:

a. oxidation of the —CH=CH— moiety to an epoxy ring, b. hydrolysis of the resulting epoxide to a mixture of said bicyclic lactone diol and a tricyclic lactone glycol, c. formolysis of said mixture to form a diformate of said bicyclic lactone diol, and d. hydrolysis of said diformate to said bicyclic lactone diol, with the proviso that, when W is cis 1-pent-2-enyl, the —C≡C— moiety is reduced to cis —CH=CH— before or after any of the steps b to d.

Reference to Chart B, herein, will make clear the transformation from the Formula-VII lactone alkene or alkenyne to diols $X_\alpha$ and $X_\beta$. Formulas VII, $X_\alpha$, $X_\beta$, XXXVIII, XXXIX, and XL, hereinafter referred to, are depicted in Chart B, wherein E and M are both hydrogen or wherein one of E and M is hydrogen and the other is formyl, wherein Y is 1-pentyl or 1-pent-2-ynyl, wherein ~ indicates attachment of the moiety to the cyclopropane ring in exo or endo configuration, or attachment of OE and OM in threo or erythro configuration, or attachment to the side chain in alpha or beta configuration, and wherein

indicates attachment of the epoxide oxygen to the side chain in alpha or beta configuration.

The Formula-VII alkene or alkenyne, prepared by steps a–f of Chart A, is transformed to epoxide XXVIII by mixing reactant VII with a peroxy compound which is hydrogen peroxide or, preferably, an organic percarboxylic acid. Examples of useful organic percarboxylic acids for this purpose are performic acid, peracetic acid, perlauric acid, percamphoric acid, perbenzoic acid, m-chloroperbenzoic acid, and the like. Peracetic acid is especially preferred.

The peroxidation is advantageously carried out by mixing the reactant VII with about one equivalent of the per acid or hydrogen peroxide, advantageously in a diluent, for example, chloroform. The reaction usually proceeds rapidly, and the Formula-XXXVIII epoxide is isolated by conventional methods, for example, evaporation of the reaction diluent and removal of the acid corresponding to the per acid if one is used. It is usually unnecessary to purify the oxide before using it in the next step.

Two procedures are available for transforming epoxide XXXVIII to diol diformate XL. In one, the epoxide is hydrolyzed to a mixture of glycol XXXIX, wherein E and M are hydrogen, and diol $X_{\alpha+\beta}$. For this purpose, a solution of dilute formic acid in an inert miscible solvent such as acetone, dimethyl sulfoxide, ethyl acetate, or tetrahydrofuran is used. Reaction temperatures of —20° C. to 100° C. may be employed, although about 25° C. is preferred. At lower temperatures, the desired mixture is produced inconveniently slowly. At higher temperatures, undesired side reactions reduce the yield of the desired mixture. Thereafter, the glycol-diol mixture is contacted with formic acid, preferably substantially 100% formic acid, at about 25° C. to form the diol formate. By "substantially 100% formic acid" is meant a purity of at least 99.5%.

In the other procedure, epoxide XXXVIII is subjected to formolysis directly. Preferably substantially 100% formic acid is used, at about 25° C. An inert solvent such as dichloromethane, benzene, or diethyl ether may be employed.

In either procedure, glycol monoformate XXXIX, wherein one of E and M is hydrogen and the other is formyl, is often present as an intermediate. It is ordinarily not isolated, but is converted to diol diformate XL in substantially 100% formic acid.

The diol diformate XL is obtained as a mixture of isomers in which the formyl group on the side chain are in the alpha and beta configurations. The mixture is converted directly to the diols $X_\alpha$ and $X_\beta$ without separation. For this purpose, the diol diformates are contacted with a weak base such as an alkali metal carbonate, bicarbonate, or phosphate, preferably sodium or potassium bicarbonate, in a lower alkanol, for example methanol or ethanol. For this base hydrolysis, a temperature range of 10° C. to 50° C. is operable, preferably about 25° C. The product is a mixture containing the diols $X_\alpha$ and $X_\beta$, wherein the hydroxyl on the side chain is in the alpha and beta configuration. Separation of the alpha and beta diols is done by known procedures. Especially useful here is chromatography, for example on silica gel or alumina.

In Chart B, there are differences in the terminal groups on the side chains of Formulas VII, XXXVIII, XXXIX, XL, $X_\alpha$ and $X_\beta$. In Formula VII, Y is limited to 1-pentyl or 1-pent-2-ynyl whereas in the other formulas W includes 1-pentyl, cis 1-pent-2-enyl, or 1-pent-2-ynyl. Similarly to Chart A above, the compounds wherein W is cis 1-pent-2-enyl are obtained by reducing the —C≡C— moiety to cis —CH=CH— by methods known in the art at any stage after the epoxidation of the —CH=CH— moiety of compound VII.

The formation of $PGE_2$ or $PGF_{2\alpha}$ from the Formula-$X_\alpha$ lactone diol intermediate is done by the steps shown in Charts C and E known in the art. See E. J. Corey et al., J. Am. Chem. Soc. 91, 5675 (1969). The Formula-XI compound is within the scope of the Formula-X diol when W is n-$C_5H_{11}$. The formation of $PGF_{2\beta}$ by carbonyl reduction of $PGE_2$ is known in the art. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, diisobutyl aluminum hydride, and when carbon-carbon double bond, especially cis, reduction is not a problem, the boranes, e.g., disiamylborane. As is known, this method gives a mixture of $PGF_{2\alpha}$ and $PGF_{2\beta}$, which are readily separated by chromatography. The formation of $PGA_2$ by acidic dehydration of $PGE_2$ is known in the art. See, for example, Pike et al., Proc. Nobel Symposium 11, Stockholm (1966), Interscience Publishers, New York, p. 162 (1967), and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration.

With regard to Formulas II to XXXIV, examples of alkyl of one to 4 carbon atoms, inclusive, are methyl, ethyl, propyl, butyl, and isomeric forms thereof. Examples of alkyl of one to 8 carbon atoms, inclusive, are those given above, and pentyl, hexyl, heptyl, octyl, and isomeric forms thereof. In Formulas XI-XVI and elsewhere, "n-C$_5$H$_{11}$" represents the normal-pentyl group, and "THP" represents the tetrahydropyranyl group.

There is further provided a process for preparing PGE$_3$, dl-PGE$_3$, or their 15-epimers, which comprises starting with an optically active glycol of the formula

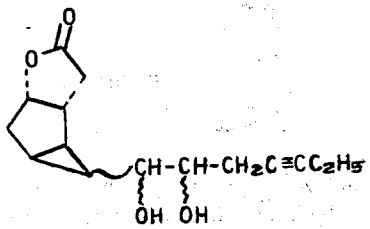

or a racemic compound of that formula and the mirror image thereof, wherein ~ indicates attachment of the moiety to the cyclopropane ring in exo or endo configuration and to the side chain in alpha or beta configuration, and subjecting said glycol successively to the following reactions:

a. replacement of the glycol hydrogens by an alkanesulfonyl group, R$_9$O$_2$S—, wherein R$_9$ is alkyl of one to 5 carbon atoms, inclusive;

b. mixing with water at a temperature in the range of 0° to 60° C. to form a bicyclic lactone diol of S and R configuration;

c. separation of said diols of S and R configuration;

d. transformation to a bis(tetrahydropyranyl) ether;

e. reduction of the lactone oxo group to a hydroxy group;

f. Wittig alkylation with a compound of the formula Hal—(CH$_2$)$_4$—COOH wherein Hal is bromo or chloro;

g. oxidation of the 9-hydroxy to oxo; and h. transformation of the two tetrahydropyranyloxy groups to hydroxy groups;

with the proviso that, before or after any of the steps a to h, the —C ≡ C— moiety is reduced to cis —CH=CH—.

Reference to Charts A and D, herein, will make clear the transformation from bicyclic aldehyde I to PGE$_3$, ent-PGE$_3$, dl-PGE$_3$, or their 15-epimers. In Chart D, Z is cis 1-pent-2-enyl or 1-pent-2-ynyl, and ~ and THP are as defined above. A key intermediate for this sequence is the racemic or optically active lactone aldehyde VI. The Formula-VI compound is prepared from racemic bicyclic aldehyde I by steps a–e of Chart A and thereafter resolved in an optically active form by the method disclosed hereinafter via the oxazolidine of Example 15. Optionally, the Formula-I aldehyde is resolved as disclosed hereinafter in Example 13, and thereafter converted to the optically active Formula-VI compound.

In carrying out step f of Chart A, the Wittig reaction is employed, using a 1-hex-2-ynyl chloride, bromide, or iodide, preferably bromide, to prepare the necessary Wittig reagent by processes known in the art.

In carrying out steps g through i of Chart A, the procedures for hydroxylating the Formula-VII alkenyne wherein Y is 1-pent-2-ynyl, forming the Formula-IX bis-(alkanesulfonic acid) ester, and hydrolyzing that ester to the Formula-X lactone diol are generally known in the art. See South African Pat. 69/4809 issued July 3, 1970. The Formula-X lactone diol, which contains both α and β epimers as produced, yields the final product as a mixture of PGE$_3$ and its 15-epimer. It is preferable that the diol α and β epimers be separated rather than the final product epimers. Silica gel chromatography is employed for this purpose. The Formula-X β-epimer then leads to the dl-15β-PGE$_3$.

In converting glycol VIII, wherein W is 1-pent-2-ynyl, to the Formula-XXII product, the —C ≡ C— moiety is reduced to cis —CH=CH— at any stage. Thus, glycol VIII is optionally reduced before replacing the glycol hydrogens with an alkanesulfonyl group; or any of the Formula-IX, -X, -XVIII, -XIX, -XX, or -XXI intermediates is optionally reduced. Reducing reagents, catalysts and conditions are used which do not substantially reduce —CH=CH—. A suitable method is to hydrogenate over a Lindlar catalyst, i.e. 5% palladium-on-barium sulfate catalyst, in the presence of quinoline. Methanol or like inert solvent or diluent is used and the pressure is low, advantageously slightly above atmospheric and ordinarily not above about two atmospheres. The resulting products are isolated by silica gel chromatography.

The formation of PGE$_3$ from the Formula-XVII diol intermediate by the steps of Chart D, other than the reduction step above-described, generally follows procedures known in th art and discussed above under the formation of PGE$_2$.

There is further provided a process for preparing PGF$_{3\alpha}$, dl-PGF$_{3\alpha}$, or their 15-epimers, in which glycol VIII, wherein W is 1-pent-2-ynyl, is transformed to diol XVII, wherein Z is cis 1-pent-2-enyl or 1-pent-2-ynyl, and thence to the Formula-XXVI products, as depicted by the steps of Chart F. Accordingly, diol XVII is reduced to lactol XXV which is then alkylated by a Wittig reaction. As in the process for PGE$_3$, the —C ≡ C— moiety is reduced to cis —CH=CH— at any stage between the glycol and the end-product. As in the process for PGE$_3$, the optical isomers of the intermediates yield the corresponding PGF$_{3\alpha}$ or ent-PGF$_{3\alpha}$; the racemic intermediates yield racemic PGF$_{3\alpha}$; the optically active α- and β-configuration intermediates yield the corresponding PGF$_{3\alpha}$, ent-PGF$_{3\alpha}$, or their 15-epimers.

The formation of racemic and optically active PGF$_{3\beta}$ from racemic and optically active PGE$_3$ generally follows procedures known in the art, e.g., by carbonyl reduction with borohydride, discussed above under the formation of PGF$_{2\beta}$. The formation of racemic and optically active PGA$_3$ from racemic and optically active PGE$_3$ likewise follows procedures known in the art, e.g., by acidic dehydration, discussed above under the formation of PGA$_2$.

There is further provided a process for resolving a racemic mixture of an oxo compound of the formula

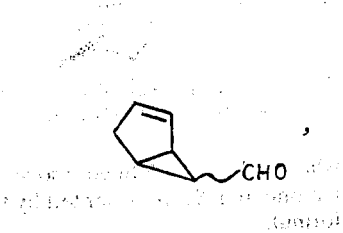
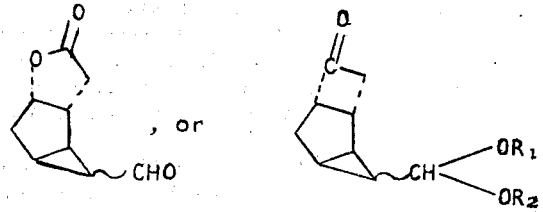

and of the mirror image thereof, wherein $R_1$ and $R_2$ are alkyl of one to 4 carbon atoms, inclusive, or, when taken together,

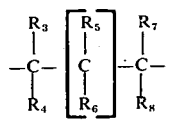

wherein $R_3$, $R_4$, $R_5$, $R_6$, and $R_8$ are hydrogen, alkyl of one to 4 carbon atoms, inclusive, or phenyl, with the proviso that not more than one of the R's is phenyl and the total number of carbon atoms is from 2 to 10, inclusive; $x$ is zero or one, and ~ indicates attachment of the moiety to the cyclopropane ring in exo or endo configuration, which comprises the steps of:

a. converting the oxo compound by reaction with an optically active ephedrine to a mixture of oxazolidine diastereomers, b. separating at least one oxazolidine diastereomer from said mixture, c. hydrolyzing said oxazolidine to free the optically active oxo compound, and d. recovering said optically active oxo compound.

In carrying out the resolution of the Formula-I bicyclic aldehyde, there is prepared an oxazolidine by reaction of the aldehyde with an optically active ephedrine, e.g. d- or l-ephedrine, or d- or l-pseudoephedrine. Approximately equi-molar quantities of the reactants are employed in a solvent such as benzene, isopropyl ether, or dichloromethane. Although the reaction proceeds smoothly over a wide range in temperature, e.g., 10°–80° C., it is preferred that it be done in the range 20° to 30° C. to minimize side reactions. With the Formula-I compound, it occurs quickly, within minutes, whereupon the solvent is removed, preferably under vacuum. The product consists of the diastereomers of the aldehyde-ephedrine product, i.e. the oxazolidines. At least one of the diastereomers is separated by methods known in the art, including crystallization and chromatography. In this instance, crystallization is used as the preferred method. Repeated recrystallization of the thus-obtained solid oxazolidine from a suitable solvent, e.g., isopropyl ether, yields one of the diastereomers in substantially pure form. The oxazolidine is then hydrolyzed by procedures known in the art to release the aldehyde. However, I have found silica gel wet with water surprisingly effective, using the silica gel in a column, with the further beneficial effect that the column acts as a means of separating the ephedrine from the aldehyde. The eluted fractions are then evaporated to yield the desired resolved Formula-I aldehyde.

The mother liquor from the recrystallized diastereomer contains the optical isomer having opposite configuration. A preferred method for isolating this second diastereomer, however, is to prepare the oxazolidine of the racemic aldehyde using ephedrine of the opposite configuration to that first employed above, and thereafter recrystallizing as above. Finally, hydrolysis and recovery yield the resolved Formula-I aldehyde in opposite configuration to that first obtained above.

I have further found that this method is generally applicable for resolving aldehydes and ketones, and is useful for resolving not only the Formula-I aldehyde but also the Formula-VI lactone aldehyde and the Formula-IV acetal ketone.

There is still further provided the new compounds produced by the above processes, all of which are useful intermediates in these processes directed toward prostaglandins, viz. bicyclic aldehyde I in its optically active forms; acetal II; mono or dihaloketone III, ketone IV; lactone acetal V; lactone aldehyde VI; the Formula-VII lactone heptene or heptenyne; lactone glycol VIII and monoformate XXXIX of the generic formula

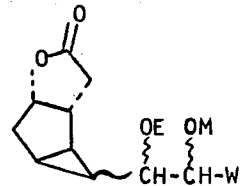

wherein E and M are both hydrogen, or wherein one of E and M is hydrogen and the other is formyl, and wherein W is 1-pentyl, cis 1-pent-2-enyl, or 1-pent-2-ynyl; the lactone bis(alkanesulfonate) IX of the formula

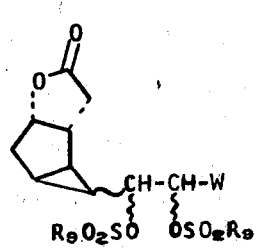

wherein $R_9$ is alkyl of one to 5 carbon atoms, inclusive, and W is as defined above;
epoxide XXXVIII of the formula

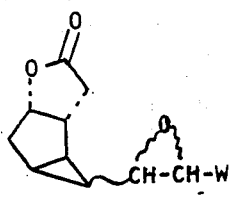

wherein W is as defined above, and wherein

indicates attachment of the epoxide oxygen to the side chain in α or β configuration;
diformate XL of the formula

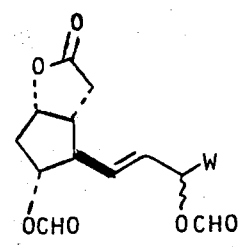

wherein W is as defined above;
lactone diol XII represented by the mirror image of the formula

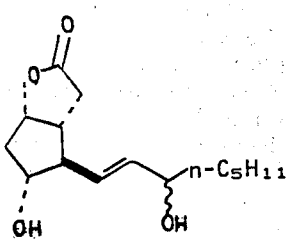

lactone diol XVII of the formula

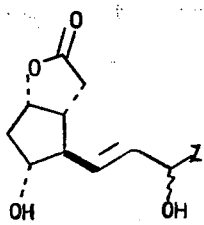

wherein Z is cis 1-pent-2-enyl or 1-pent-2-ynyl; tetrahydropyranyl lactone XVIII of the formula

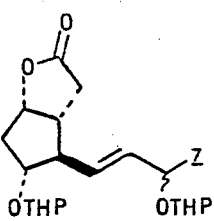

wherein THP is tetrahydropyranyl and Z is as defined above;
tetrahydropyranyl lactol XIX of the formula

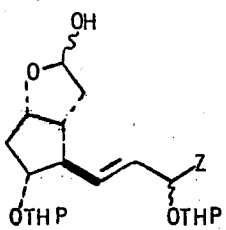

wherein THP and Z are as defined above;
a Formula-XX compound of the formula

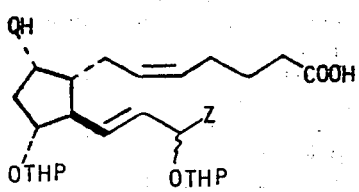

wherein THP and Z are as defined above; and oxazolidine of bicyclic aldehyde I, ketone IV, or lactone aldehyde VI with an optically active ephedrine. In these compounds indicates attachment to the cyclopropane ring in exo or endo configuration and to the side-chain in $\alpha$ (S) or $\beta$ (R) configuration. There are also provided the enantiomorphs and the racemic mixtures of the above compounds.

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60 spectrophotometer in deuterochloroform solutions with tetramethylsilane as an internal standard (downfield).

Circular dichroism curves are recorded on a Cary 60 recording spectropolarimeter.

The collection of chromatographic eluate fractions starts when the eluent front reaches the bottom of the column.

"Brine," herein, refers to an aqueous saturated sodium chloride solution.

PREPARATION 1

Endo-bicyclo[3.1.0]hex-2-ene-6-carboxaldehyde
(Formula 1: ~ is endo).

To a rapidly stirred suspension of anhydrous sodium carbonate (318 g.) in a solution of bicyclo [2.2.1] hepta-1,5-diene (223.5g.) in dichloromethane (1950 ml.) is added 177 ml. of 25.6% peracetic acid containing 6 g. of sodium acetate. The addition time is about 45 min., and the reaction temperature is 20°–26° C. The mixture is stirred for an additional 2 hrs. The reaction mixture is filtered and the filter cake washed with dichloromethane. The filtrate and washings are concentrated under vacuum. About 81 g. of the resulting liquid is stirred with 5 ml. of acetic acid in 200 ml. of dichloromethane for 5.5 hrs., then concentrated and distilled. The fraction boiling at 69°–73° C./30 mm. represents the desired Formula-I aldehyde, 73 g. NMR peaks at 5.9 and 9.3 (doublet) $\delta$.

The various Formula-I-to-IX intermediates, hereinafter, exist in exo as well as endo forms. A preferred route to the exo form of the Formula-I bicyclic aldehyde is by the steps steps shown in Chart G, using methods known in the art. See South African Pat. 69/4809 issued July 3, 1970. In Formulas XXVII to XXXVII, the attachment to the cyclopropane ring by a straight line extended downward at an angle to the right indicates the exo configuration. Thus, diazoacetic acid is added to a double bond of cyclopentadiene to give an exo-endo mixture of the Formula-XXVIII bicyclo [3.1.0]-hexene substituted at the 6-position with a carboxyl. The exo-endo mixture is treated with a base to isomerize the endo isomer in the mixture to more of the exo isomer. Next the carboxyl group at 6 is transformed to an alcohol group and thence to the exo aldehyde of the Formula XXX.

EXAMPLE 1 dl-Endo-bicyclo[3.1.0]hex-2-ene-6-carboxaldehyde Acetal of Ethylene Glycol (Formula II: $R_1$ and $R_2$ taken together are —$CH_2CH_2$— and ~ is endo).

Refer to Chart A. A solution of Formula-I endo-bicyclo[3.1.0]hex-2-ene-6-carboxaldehyde (216 g., Preparation 1), ethylene glycol (150 g.), and p-toluenesulfonic acid (0.5 g.) in benzene (1 l.) is heated under reflux. The azeotropically distilled water (29 ml. after 20 hrs.) is collected in a Dean-Stark trap. The reaction mixture is cooled, treated with sodium carbonate (0.3 g.), and distilled at reduced pressure. The fraction collected at 55°–60° C./3–4 mm. is partitioned between ether and water. The ether layer is extracted with water, dried over anhydrous magnesium sulfate, and concentrated to the Formula-II bicyclic acetal, a light tan oil (70 g.); NMR peaks at 1.1, 1.6–2.9, 3.5–4.2, 4.42, and 5.3–6.0 δ.

CHART G

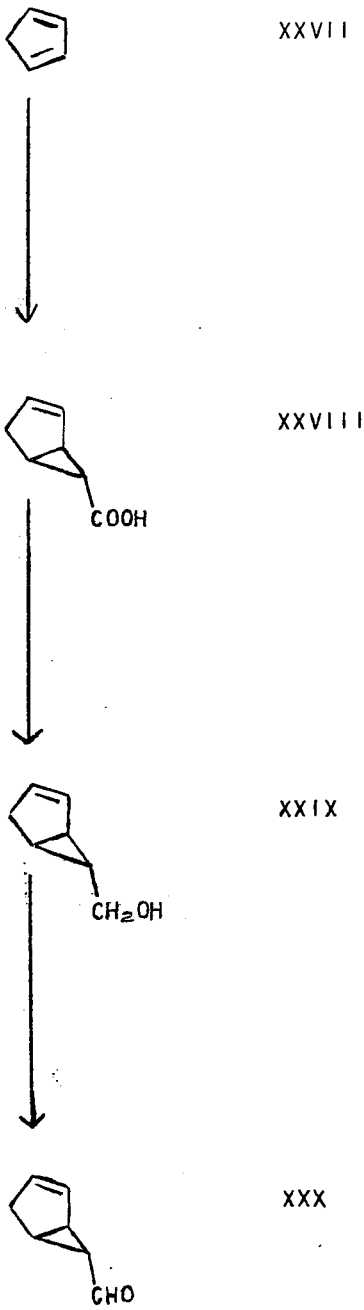

Following the procedures of Example 1 but using the exo Formula-I (XXX) compound, there is obtained the corresponding exo Formula-II acetal.

Following the procedures of Example 1 but using either the endo or exo form of the Formula-I aldehyde and substituting for the ethylene glycol one of the following glycols: 1,2-propanediol, 1,2-hexanediol, 1,3butanediol, 2,3-pentanediol, 2,4-hexanediol, 3,4-octanediol, 3,5-nonanediol, 2,2-dimethyl-1,3-propanediol, 3,3-dimethyl-2,4-heptanediol, 4-ethyl-4-methyl-3,5-heptanediol, phenyl-1,2-ethanediol and 1-phenyl-1,2-propanediol, there are obtained the corresponding Formula-II acetals.

Following the procedures of Example 1 but using either the endo or exo form of the Formula-I aldehyde and substituting for the ethylene glycol one of the following alcohols: methanol, ethanol, 1-propanol, or 1-butanol, there are obtained the corresponding Formula-II acetals.

EXAMPLE 2 dl-Tricyclic Dichloroketone (Formula III: $R_1$ and $R_2$ taken together are $-CH_2CH_2-$ and $\sim$ is endo).

Refer to Chart A. A solution of the Formula-II bicyclic acetal of Example 1 (56 g.) and triethylamine (80 g.) in 300 ml. of isomeric hexanes (Skellysolve B) is heated at reflux, with stirring, and treated dropwise with dichloroacetyl chloride (100 g.) in Skellysolve B over a 3-hour period. The mixture is cooled and filtered to remove solids. The filtrate and combined Skellysolve B washes of the filtered solid is washed with water, 5% aqueous sodium bicarbonate, and brine, dried over anhydrous sodium sulfate and concentrated to the title compound, a dark brown oil (91 g.). An additional quantity (13 g.) is recovered from the filter cake and aqueous washes. Alternatively, the triethylamine is added to a solution of the bicyclic acetal and the dichloroacetyl chloride, or the triethylamine and the dichloroacetyl are added separately but simultaneously to a solution of the bicyclic acetal in Skellysolve B.

Following the procedures of Example 2 but using the exo Formula-II compound, there is obtained the corresponding exo Formula-III tricyclic dichloroketone.

Following the procedures of Example 2, but using the Formula-II compounds disclosed following Example 1, there are obtained the corresponding Formula-III compounds.

EXAMPLE 3 dl-Tricyclic Ketone (Formula IV: $R_1$ and $R_2$ are methyl and $\sim$ is endo).

A solution of the Formula-III dichloroketone of Example 2 (104 g.) in dry methanol (1 l.) is treated with ammonium chloride (100 g.) and small portions of zinc dust. The temperature is allowed to rise to 60° C. After 200 g. of zinc have been added, the mixture is heated under reflux for an additional 80 min. The mixture is cooled, the solids filtered off, and the filtrate concentrated. The residue is treated with dichloromethane and 5% aqueous sodium bicarbonate and the mixture is filtered. The dichloromethane layer is washed with 5% aqueous sodium bicarbonate and water, dried, and concentrated to the title compound, a dark brown oil (56 g.); infra-red absorption at 1760 cm$^{-1}$.

Following the procedures of Example 3 but using the exo Formula-III compound, there is obtained the corresponding exo Formula-IV tricyclic ketone.

Following the procedures of Example 3 but using the Formula-III compounds disclosed following Example 2, there are obtained the corresponding Formula-IV compounds.

EXAMPLE 4 dl-Tricyclic Lactone Acetal (Formula V: $R_1$ and $R_2$ are methyl and $\sim$ is endo), and Tricyclic Lactone Aldehyde (Formula VI: $\sim$ is endo).

Refer to Chart A. A solution of the Formula-IV product of Example 3 (56 g.) in dichloromethane (400 ml.) is treated with potassium bicarbonate (40 g.) and cooled to 10° C. A solution of meta-chloroperbenzoic acid (55 g. of 85%) in dichloromethane (600 ml.) is added over 40 min. The mixture is stirred at 10° C. for 1 hr., then warmed to reflux for 40 min. The mixture is cooled and filtered, and the filtrate is washed with 5% aqueous sodium bicarbonate-sodium thiosulfate, and then water. The dichloromethane layer is dried over anhydrous sodium sulfate, and concentrated to the Formula-V acetal (61 g.). A portion (58 g.) is chromatographed on 2 kg. of silica gel packed in ethyl acetate Skellysolve B (50-50). Elution with 50-50, 70-b 30 and 80-20 ethyl acetate-Skellysolve B yields a fraction (24.9 g.) shown by NMR to be a mixture of dimethyl acetal (V) and aldehyde (VI). A portion (22.6 g.) of the mixture is dissolved in 100 ml. of (60-40) formic acid-water and allowed to stand 1 hr. at 25° C. The solution is then concentrated under vacuum and the residue taken up in dichloromethane. The dichloromethane solution is washed with 5% aqueous sodium bicarbonate and water, dried over sodium sulfate, and concentrated to a brown oil (17.5 g.) which crystallizes on seeding. Trituration of the crystals with benzene leaves crystals of the Formula-VI aldehyde (9.9 g.). An analytical sample is obtained by recrystallization from tetrahydrofuran, m.p. 72°–74° C. (corr.); infrared absorption peaks at 2740, 1755, 1710, 1695, 1195, 1165, 1020, 955, and 910, cm$^{-1}$; NMR peaks at 1.8–3.4, 5.0–5.4, and 9.92 $\delta$.

Following the procedures of Example 4 but using the exo Formula-IV lactone acetal compound, there is obtained the corresponding exo Formula-V lactone acetal.

Likewise, following the procedures of Example 4 using the exo Formula-V compound, there is obtained the corresponding exo Formula-VI lactone aldehyde.

Following the procedures of Example 4 but using the Formula-IV compounds disclosed following Example 3, there are obtained the corresponding Formula-V compounds, and, thence, the corresponding Formula-VI lactone aldehydes.

EXAMPLE 5 dl-Tricyclic Lactone Heptene (Formula VII: Y is 1-pentyl and ~ is endo).

Refer to Chart A. A suspension of n-hexyltriphenylphosphine bromide (6.6 g.) in 20 ml. of benzene is stirred under nitrogen and to it is added 10 ml. of 1.6 m. n-butyl-lithium in n-hexane. After 10 min. a benzene solution of the Formula-VI tricyclic aldehyde (1.66 g.) of Example 4 is added dropwise over 15 min. and the reaction mixture is heated at 65°–70° C. for 2.5 hrs. The mixture is cooled, the solids are filtered off and washed with benzene, and the combined filtrate and washes are extracted with dilute hydrochloric acid and water. The solution is dried over sodium sulfate and concentrated under vacuum to an oil (3.17 g.). The crude Formula-VII product is chromatographed on 400 g. of silica gel packed with (30–70) ethyl acetatecyclohexane and eluted with the same mixture. Fractions of 20 ml. volume are collected. Fractions 47–50 are found to contain 0.8 g. of the desired Formula-VII tricyclic lactone heptene; NMR peaks at 0.6–3.0, 4.4– 5.1, and 5.4 $\delta$. To minimize side reactions, it is preferred that the Wittig reagent prepared from the phosphonium bromide and n-butyl-lithium be filtered to remove lithium bromide, and that the resultant solution be added to the benzene solution of the Formula-VI tricyclic aldehyde in equivalent proportions.

Following the procedures of Example 5 but using the exo Formula-VI compound, there is obtained the corresponding exo Formula-VII lactone heptene. A preferred source of the exo form of the Formula-VI tricyclic lactone aldehyde is by the steps shown in Chart H. Therein R$_{14}$ is alkyl of one to 4 carbon atoms. Thus, diazoacetic acid ester is added to a double bond of cyclopentadiene to give an exo-endo mixture of the Formula-XXXI bicyclo[3.1.0]hexene substituted at 6 with an esterified carboxyl, e.g. a methyl ester wherein R$_{10}$ is methyl. The exo-endo mixture is treated with a base to isomerize the endo isomer to more of the exo isomer. Next the hexene is reacted with Cl$_2$C=C=O generated in situ from dichloroacetyl chloride and a tertiary amine or from trichloroacetyl chloride and zinc dust as in step $b$ of Chart A, to the Formula-XXXII dichloroketone. Successively, the dichloroketone is reduced as in step $c$ of Chart A; the resulting Formula-XXXIII tricyclic ketone is converted to a lactone ester as in step $d$ of Chart A; the lactone is saponified, then acidified, to yield the Formula-XXXV compound with a carboxyl group at the 6-position; then the carboxyl group is transformed to an alcohol group and finally to the exo aldehyde of Formula XXXVII.

CHART H

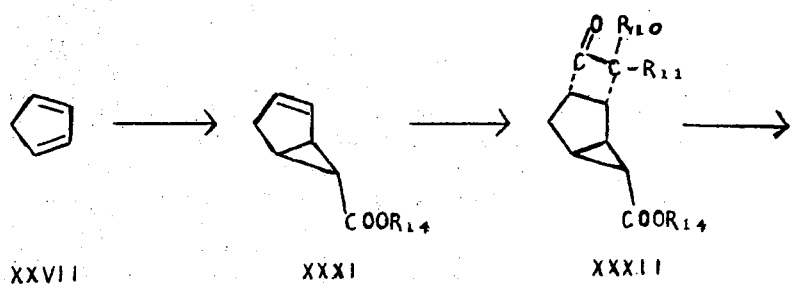

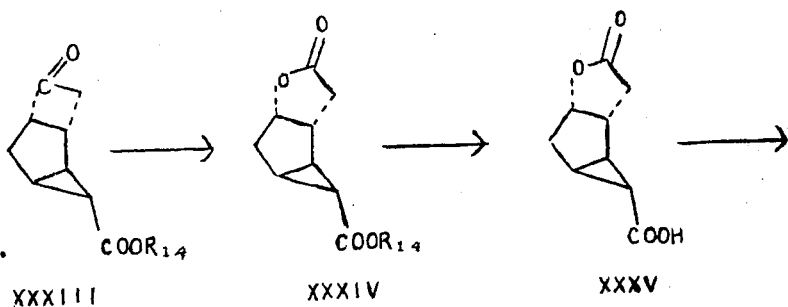

XXXIII → XXXIV → XXXV →

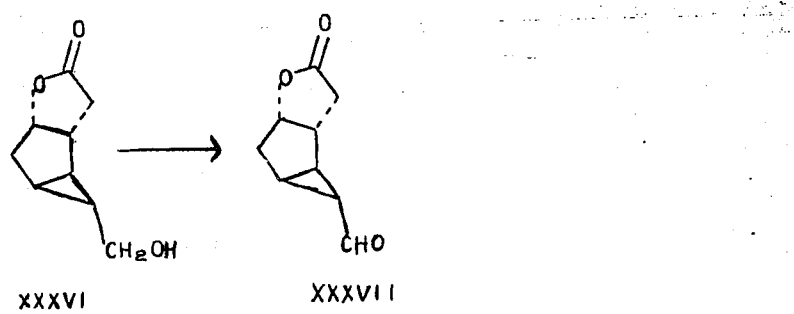

XXXVI → XXXVII

EXAMPLE 6 dl-Tricyclic Glycols (Formula VIII: W is 1-pentyl and ~ is endo). Refer to Chart A.

Procedure A. A solution of the Formula-VII tricyclic lactone heptene of Example 5 (0.8 g.) in 10 ml. of benzene is treated with osmium tetroxide (1.0 g.) in 15 ml. of benzene. After standing 24 hrs., the mixture is treated with hydrogen sulfide for 30 min., then filtered to remove a black solid. The filtrate is evaporated to an oil (393 mg.). An additional quantity of oil (441 mg.) is recovered by suspending the black solid in ethyl acetate and again treating with hydrogen sulfide. The oil is chromatographed on 100 g. of silica gel packed and eluted with (40–60) acetone-dichloromethane. Fractions of 20 ml. volume are collected. Two erythro glycols of Formula VIII are recovered, one more polar (slower-moving on the column) than the other. The faster-moving glycol, 0.3 g., is found in fractions 20–30; the slower-moving one, 0.28 g., in fractions 31– 40.

Procedure B. A mixture of 7 ml. of N-methylmorpholine oxide-hydrogen peroxide complex (see Fieser et al., "Reagents for Organic Syntheses," p. 690, John Wiley and Sons, Inc., New York, N.Y. (1967)), 8 ml. of THF, 14 ml. of tert-butanol, and osmium tetroxide (2mg.) in 2 ml. of tert-butanol is cooled to about 15° C.

A solution of the Formula-VII tricyclic lactone heptene of Example 5 (3.95 g.) in 12 ml. of THF and 12 ml. tert-butanol is then added slowly over a period of 2 hrs. at a temperature of 15°–20° C. The mixture is stirred for an additional 2 hrs., and to it is added a slurry of filter aid (for example magnesium silicate, 0.8 g.) in 14 ml. of water containing sodium thiosulfate (0.4 g.), and the solids removed by filtration. The filtrate is concentrated under reduced pressure to an oil. Water (200 ml.) is added and the oil-water mixture is extracted with several portions of dichloromethane. The dichloromethane solution is dried over magnesium sulfate and then concentrated under reduced pressure to a mixture containing the title products.

Following the procedures of Example 6A and 6B but using the exo Formula-VII compound, there are obtained the corresponding exo Formula-VIII tricyclic glycols.

EXAMPLE 7 dl-Bicyclic Lactone Bismesylate (Formula IX: $R_9$ is methyl, W is 1-pentyl, and ~ is endo), and Bicyclic Lactone Diol (Formula X: W is 1-pentyl and ~ indicates the α configuration.

Refer to Chart A. The slower moving Formula-VIII erythro glycol from Example 6 (277 mg.) is dissolved in 5 ml. of pyridine, cooled to 0° C. under nitrogen, and treated with methanesulfonyl chloride (0.89 g.). The mixture is stored at 0° C. for 20 hrs., ice water (0.6 ml.) is added and the mixture stirred an additional 20 min. Then the mixture is poured into dichloromethane and washed with ice-cold 1 N. hydrochloric acid, ice-cold 5% sodium bicarbonate solution, and ice water. The solution is dried and concentrated under vacuum to an oil (290 mg.), consisting of the Formula IX bis-mesylate compound.

The above product is dissolved in 10 ml. of acetone and 5 ml. of water, left standing for 3 hrs. at 25° C., and concentrated under reduced pressure to remove the acetone. The solution is diluted with water and extracted with dichloromethane. The dichloromethane solution is washed with 5% sodium bicarbonate solution and brine, dried, and concentrated under vacuum to an oil (200 mg.), consisting of the Formula-X product.

The Formula-X compound is obtained as a mixture of isomers in the α and β configuration. They are separated by silica gel chromatography and are used separately, e.g. in preparing the Formula-XII bis(tetrahydropyranyl) ether. The undesired Formula-X isomer is recycled to isomerize it to a mixture of the α and β forms. For the isomerization, the 15-hydroxyl is oxidized to a 15-keto with selective oxidant, e.g., 2,3-dichloro-5,6-dicyano-1,4-benzoquinone, activated manganese dioxide, or nickel peroxide (see Fieser et al., "Reagents for Organic Syntheses," John Wiley and Sons, Inc., New York, N.Y., pp. 215, 637, and 731). Thereafter, the 15-keto compound is reduced with zinc borohydride, by methods known in the art, to a mixture of the α and β isomers, which are then separated by silica gel chromatography.

Following the procedure of Example 7, the faster-moving glycol is transformed to the same Formula-X product as above.

Following the procedures of Example 7 but using the exo Formula-VIII compound, there is obtained the corresponding exo Formula-IX bismesylate. This exo bismesylate is transformed to the Formula-X lactone diol by the procedures of Example 7 used for the endo compound.

The Formula-X lactone diol wherein W is 1-pentyl is transformed to dl-PGE$_2$ ]and dl-PGF$_{2\alpha}$ and their alkyl esters using methods generally known in the art, e.g., following the steps of Chart C for dl-PGE$_2$ and Chart E for dl-PGF$_{2\alpha}$.

EXAMPLE 8 dl-Endo-bicyclo[3.1.0]hex-2-ene-6-carboxaldehyde Acetal of 2,2-dimethyl-1,3-propanediol (Formula II: R$_1$ and R$_2$ taken together are $-CH_2-C(CH_3)_2-CH_2-$ and ~ is endo).

Refer to Chart A. A solution of Formula-I endobicyclo[3.1.0]hex-2-ene-6-carboxaldehyde (48.6 g.), 2,2-dimethyl-1,3-propanediol (140.4 g.), and oxalic acid (0.45 g.) in benzene (0.9 l.) is heated under reflux for 4 hrs. The azeotropically distilled water is removed in a water separator. The reaction mixture is cooled, washed with 5% sodium bicarbonate solution and water. The benzene solution is dried over sodium sulfate, concentrated to an oil (93 g.), and distilled at reduced pressure. The fraction boiling at 88°–95° C./0.5 mm. is the desired title compound, 57.2 g., m.p. 53°–55° C.; NMR peaks at 0.66, 1.2, 3.42, 3.93, and 5.6 δ; infrared absorption at 1595, 1110, 1015, 1005, 990, 965, 915 and 745 cm$^{-1}$.

Following the procedure of Example 8 but using the exo Formula-I compound, there is obtained the corresponding exo Formula-II acetal.

EXAMPLE 9 d7-Tricyclic Dichloroketone (Formula III: R$_1$ and R$_2$ taken together are $-CH_2-C(CH_3)_2-CH_2-$ and ~ is endo).

Refer to Chart A. Following the procedures of Example 2, the Formula-II compound of Example 8 is transformed to the title compound, m.p. 97°–100° C., NMR peaks at 0.75, 1.24, 2.43 (multiplet), 3.42, 3.68, and 3.96 (doublet) δ; infrared absorption at 3040, 1810, 1115, 1020, 1000, 980, 845, and 740 cm$^{-1}$.

EXAMPLE 10 dl-Tricyclic Ketone (Formula IV: R$_1$ and R$_2$ taken together are $-CH_2-C(CH_3)_2-CH_2-$ and ~ is endo).

Refer to chart A. Following the procedure of Example 3, the Formula-III dichloroketone of Example 9 is transformed to the title compound, an oil; NMR peaks at 0.75, 1.25, 3.0 (multiplet) and 4.0 (doublet) δ; infrared absorption at 1170 cm$^{-1}$.

Following the procedures of Examples 3 and 10 but using the corresponding exo Formula-III compound, there is obtained the corresponding exo Formula-IV tricyclic ketone.

EXAMPLE 10A dl-Tricyclic Lactone Acetal (Formula V: R$_1$ and R$_2$ taken together are $-CH_2-C(CH_3)_2-CH_2-$ and ~ is endo) and Tricyclic Lactone Aldehyde (Formula VI: ~ is endo).

Refer to chart A. Tricyclic ketone IV (Example 10, 12 g.) together with potassium bicarbonate (6.1 g.) in 100 ml. of dichloromethane is cooled to about 10° C. Metachloroperbenzoic acid (12.3 g. of 85%) is added portionwise at such a rate that the reaction temperature is kept below 30° C. Thereafter the mixture is stirred for 1 hr. and to it is added 150 ml. of 5% aqueous sodium bicarbonate solution containing 9 g. of sodium thiosulfate. The dichloromethane layer is dried over sodium sulfate and concentrated under reduced pressure. The oily residue contains the Formula-V lactone acetal: NMR peaks at 0.75, 1.23, 3.5 (quartet), 3.9 (doublet) and 4.8 (quartet) δ; infrared absorption at 1760 cm$^{-1}$.

Lactone acetal V (about 4.4 g.) in 60 ml. of 88% formic acid is left standing at 50° C. for one hour. The solution is then cooled, diluted with 60 ml. of 1 N. sodium hydroxide saturated with sodium chloride, and extracted with dichloromethane. The combined extracts are washed with 10% sodium carbonate, dried over sodium sulfate, and concentrated under reduced pressure. The product crystallizes on standing, yielding the Formula-VI lactone aldehyde: m.p. 69°–73° C., NMR peaks at 5.2 (multiplet) and 10.0 (doublet) δ, and infrared absorption at 1755 cm$^{-1}$.

Following the procedures of Example 10A, the corresponding exo Formula-IV tricyclic ketone yields the corresponding Formula-V and -VI compounds.

EXAMPLE 11 dl-PGE$_3$, dl-15-epi-PGE$_3$, and their Alkyl Esters (Formula XXII of Chart D: ~ indicates the 15α or 15β configuration).

Refer to Charts A and D. Following the procedures of Examples 1–4, inclusive, the endo Formula-I bicyclohexene aldehyde is transformed to the endo Formula-VI tricyclic lactone aldehyde.

Following the procedure of Example 5, but substituting for the n-hexyltriphenylphosphine bromide the unsaturated phosphonium compound derived from 1-bromo-3-hexyne, viz. 1-hex-3-ynyltriphenylphosphine bromide, there is obtained the Formula-VII heptenyne compound wherein Y is 1-pent-2-ynyl and ~ is endo.

Successively, following the procedures of Examples 6 and 7, there are formed the Formula-VIII, -IX, and -X compounds wherein W is 1-pent-2-ynyl and ~ is endo for the moiety on the cyclopropane ring, and represents either the α or β configuration for the hydroxyl group on the sidechain. The Formula-X octenyne diol is obtained as a mixture of isomers in the α and β configuration. They are separated by silica gel chromatography and are used in preparing the Formula-XVII compounds. The undesired Formula-X isomer is recycled and isomerized using the procdures of Example 7. The α-configuration Formula-X ocetenyne diol wherein W is 1-pent-2-ynyl is reduced to the Formula-XVII octadiene diol wherein Z is 1-pent-2-enyl by reducing the —C ≡ C— moiety to cis —CH=CH— by hydrogenation over Lindlar catalyst as follows. To a solution of the Forumula-X compound (20 mg.) in methanol (2 ml.) is added 5 mg. of 5% palladium-on-barium sulfate and 2 drops of synthetic quinoline. The mixture is stirred at about 25° C. and atmospheric pressure. The reaction is terminated when one equivalent of hydrogen is absorbed. The mixture is filtered and the filtrate concentrated under vacuum. Ethyl acetate is added and the solution is chromatographed on silica gel impregnated with silver nitrate. The column is developed with isomeric hexanes (Skellysolve B) containing increasing amounts of ethyl acetate. Those fractions containing the desired octadiene diol are combined and concentrated to yield the Formula-XVII intermediate.

Following the steps of Chart D, the Formula-XVII compound, wherein Z is 1-pent-2-enyl and ~ represents the α configuration, is transformed to $PGE_3$ using methods generally known in the art. Thus, the Formula-XVII diol is converted to the Formula-XVIII bis(-tetrahydropyranyl) ether; the oxo group of the lactone is reduced to form the Formula-XIX lactol; the Formula-XX compound is formed by a Wittig reaction using ω-chloro or ω-bromopentanoic acid; the Formula-XX 9-hydroxy group is oxidized to the 9-keto group of the Formula-XXI intermediate; and, finally, the protective tetrahydropyranyl groups are removed by hydrolysis to yield the desired Formula-XXII dl-$PGE_3$.

Following the procedures of Example 11, but substituting the exo Formula-I aldehyde for the endo aldehyde, there are obtained the Formula-VI, -VII, -VIII and -IX exo compounds which are converted to the Formula-X lactone diol, and thence to dl-$PGE_3$.

Following the procedures of Example 11 for dl-$PGE_3$, but substituting the 15β (R)-configuration Formula-X octenyne diol for the S-configuration compound, there are formed any of the Formula-XVII-to-XXI intermediates wherein ~ indicates the β configuration, and thence dl-15β-$PGE_3$ of Formula-XXII wherein ~ indicates the β configuration.

Although Example 11 illustrates one embodiment of the process for preparing $PGE_3$, wherein the —C ≡ C— moiety of the Formula-X octenyne diol is reduced to cis —CH=CH— immediately before forming the cis(tetrahydropyranyl) ether, it is within the scope of this invention as shown in Charts A and D to carry out that reduction of —C ≡ C— to cis —CH=λ CH— at any stage between the Formula-VIII glycol and the final dl-$PGE_3$ or dl-15β-$PGE_3$.

Thus, the Formula-VIII compound wherein W is 1-pent-2-ynyl and ~ indicates attachment of the moiety to the cyclopropane ring in exo or endo configuration, is subjected successively to the following reactions:

a. replacement of the glycol hydrogens by an alkanesulfonyl group, $R_9O_2S$—, wherein $R_9$ is alkyl of one to 5 carbon atoms, inclusive;

b. mixing with water at a temperature in the range of 0° to 60° C. to form a bicyclic lactone diol;

c. separation of the diols of α (S) and β (R) configuration;

d. transformation to a bis(tetrahydropyranyl) ether;

e. reduction of the lactone oxo group to a hydroxy group;

f. Wittig alkylation with a compound of the formula Hal—$(CH_2)_4$—COOH wherein Hal is bromo or chloro;

g. oxidation of the 9-hydroxy to oxo; and h. transformation of the two tetrahydropyranyloxy group to hydroxy groups;

with the proviso that, before or after any of the steps a to h, the —C ≡ C— moiety is reduced to cis —CH=λ CH—, thereby forming dl-$PGE_3$ or dl-15β-$PGE_3$. By these procedures, there are formed the intermediates of Formulas VIII, IX, and X, wherein W is either cis 1-pent-2-enyl or 1-pent-2-ynyl; and the intermediates of Formulas XVIII, XIX, XX, and XXXI, wherein Z is either cis 1-pent-2-enyl or 1-pent-2ynyl.

EXAMPLE 12 dl-$PGF_{3\alpha}$ and dl-15-epi-$PGF_{3\alpha}$ Esters (Formula XXVI of Chart E: ~ indicates the 15α (S) or 15β (R) configuration).

Refer to Chart E. Following the procedures of Example 11, there is prepared the α-configuration Formula-XVII octadiene diol. This diol is transformed to $PGF_{3\alpha}$ by the steps shown in Chart E wherein ~ indicates the α configuration, using methods known in the art. Thus, the Formula- XVII diol is converted to the Formula-XXV lactol by reducing the oxo group of the lactone; and the Formula-XXV compound is converted to dl-$PGF_{3\alpha}$ (Formula XXVI wherein ~ indicates the S configuration) by a Wittig reaction using ωchloro- or ω-bromo-pentanoic acid.

Following the procedures of Example 12, but substituting the β-configuration Formula-XVII octadiene diol for the α-configuration Formula-XVII octadiene diol, there is obtained dl-15β-$PGF_{3\alpha}$ (Formula XXVI wherein ~ indicates the β configuration).

Although Example 22 illustrates one embodiment of the process for preparing $PGF_{3\alpha}$, wherein the —C ≡ C— moiety of the Formula-X octenyne diol is reduced to cis —CH=CH— immediately before reducing the lactone oxo group to a hydroxy group, it is within the scope of this invention as shown in Charts A and F to carry out the reduction of —C ≡ C— to cis —CH=CH— at any stage between the Formula-VIII glycol and the final dl-$PGF_{3\alpha}$ and dl-15β-$PGF_{3\alpha}$. Thus, the Formula-VIII compound wherein W is 1-pent-2-ynyl and ~ indicates attachment of the moiety to the cyclopropane ring in exo or endo configuration is subjected successively to the following reactions:

a. replacement of the glycol hydrogens by an alkanesulfonyl group, $R_9O_2S$—, wherein $R_9$ is alkyl of one to 5 carbon atoms, inclusive;

b. mixing with water at a temperature in the range of 0° to 60° C. to form a bicyclic lactone diol;

c. separation of the diols of α and β configuration;

d. reduction of the lactone oxo group to a hydroxy group; and e. Wittig alkylation with a compound of the formula Hal—$(CH_2)_4$—COOH wherein Hal is bromo or chloro; with the proviso that, before or after any of the steps a to e, the —C ≡ C— moiety is reduced to cis —CH=λ Ch—, thereby forming dl-$PGF_{3\alpha}$ or dl-15β-$PGF_{3\alpha}$. By these procedures, there is formed the Formula-XXV intermediate wherein Z is either cis 1-pent-2-enyl or 1-pent-2-ynyl.

EXAMPLE 13

Resolution of
Endo-bicyclo[3.1.0]hex-2-ene-6-carboxaldehyde
(Formula 1: ~ is endo).

A. Formula-I endo-bicyclo[3.1.0]hex-2-ene-6-carboxaldehyde (12.3 g.) and l-ephedrine (16.5 g.) are dissolved in about 150 ml. of benzene. The benzene is removed under vacuum and the residue taken up in about 150 ml. of isopropyl ether. The solution is filtered, then cooled to −13° C. to yeild crystals of 2-endo-bicyclo[3.1.0]hex-2-en6-yl-3,4-dimethyl-5-phenyl-oxazolidine, 11.1 g., m.p. 90°–92° C. Three recrystallizations from isopropyl ether, cooling each time to about −2° C., yield crystals of the oxazolidine, 2.2 g., m.p. 100°–103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatography-grade, (Merck), 0.05–0.2 mm. particle size, with about 4–5 g. water per 100 g. Fractions of the eluate are collected, and those shown by thin layer chromatography (TLC) to contain the desired compound are combined and evaporated to an oil (360 mg.). This oil is shown by NMR to be desired Formula-I compound, endo-bicyclo[3.1.0]hex-2-ene-6-carboxaldehyde, substantially free of the ephedrine, in substantially a single opticallyactive isomeric form; called "the isomer of Example 13-A" herein. Points on the circular dichroism curve are ($\lambda$ in nm, $\theta$): 350, 0; 322.5, −4,854; 312, −5,683; 302.5, −4,854; 269, 0; 250, 2,368; 240, 0; and 210, −34,600.

B. The mother liquors of the oxazolidine are combined and evaporated to crystals, taken up in dichloromethane, and chromatographed on silica gel as above to yield the enantiomorph of the above Formula-I compound, having the opposite optical rotation.

C. A preferred method of obtaining the isometic oxazolidine which yields the aldehyde of optical rotation opposite to that of the isomer of Example 13-A is as follows. Following the procedure of A, above, the racemic aldehyde is reacted with d-ephedrine to produce the oxazolidine in its diastereomeric forms. Recrystallization then yields the desired oxazolidine, which is converted by hydrolysis to the desired optically active aldehyde.

Following the procedures of Example 13, the exo Formula-I bicyclo[3.1.0]hex-2-ene-6-carboxaldehyde is converted to the oxazolidine of d- or l-ephedrine and resolved into its optically active isomers.

EXAMPLE 14

Resolution of Acetal Ketone (Formula IV: $R_1$ and $R_2$ taken together are —$CH_2$—$C(CH_3)_2$—$CH_2$— and ~is endo).

A. A solution of 2.34 g. of the Formula-IV acetal ketone of Example 10 (wherein the acetal is prepared from 2,2-dimethyl-1,3-propanediol) and l-ephedrine (1.65 g.) in benzene (15 ml.), together with 1 drop of acetic acid, is heated at reflux for about 5.5 hrs., using a Dean and Stark trap to remove water. The benzene is then removed by evaporation leaving the formed oxazolidine as solids which are dissolved in methanol. On cooling the methanol solution, there is obtained one of the diastereomeric oxazolidines, 1.57 g., m.p. 161°–166° C. [$\alpha_D^{25}$ −7.5° in chloroform, now substantially a single isomeric form as shown by NMR. NMR peaks at 0.63 (doublet), 0.72, 1,23, 2,38, 3,52, 3,95 (doublet) and 4.94 (doublet) $\delta$ Following the procedure of Example 13, the above crystallized oxazolidine is converted on a silica gel column to an optically active isomer of the desired Formula-IV compound, 0.56 g., m.p. 43°–47° C. [$\alpha]_D^{25}$ +83° in chloroform; called "the isomer of Example 14-A" herein.

B. The mother liquor from A is concentrated and chilled to −13° C., to yield another diastereomeric oxazolidine, 1.25 g., m.p. 118°–130° C., [$\alpha]_D^{25}$ +11.7° in chloroform; NMR peaks at 0.63 (doublet), 0.72, 1.23, 2.38, 3.52, 3,99 (doublet) and 5.00 (doublet) $\delta$.

Following the procedure of Example 13, the crystallized oxazolidine is converted on a silica gel column to an optically active isomer of the Formula-IV compound.

C. Reaction of the above Example 14–B isomer with d-ephedrine by the procedure of Example 14-A yields the enan-tiomorph of the oxazolidine of Example 14A, m.p. 165° C., [$\alpha]_D^{25}$ +7.5° in chloroform.

Following the procedure of Example 13, the crystallized oxazolidine is converted on a silica gel column to an optically active isomer of the desired Formula-IV identical to that obtained in Example 14–B above.

Following the procedures of Example 14, the exo Formula-IV acetal ketone of Example 10 is converted to the oxazoldine of d- or l-ephedrine and resolved into its optically active isomers.

Any one of the above resolved oxazolidines is hydrolyzed to the oxo compound and ephedrine by contact with water, preferably with an acid catalyst, as is known in the art (see Elderfeld, Heterocyclic Compounds, Vol. 5, page 394, Wiley, N.Y., 1957). Thus, the oxazolidine of l-ephedrine and the Formula-IV acetal ketone (Example 14A, 5.0 g.) is stirred in a solution of tetrahydrofuran-water-acetic acid (25 ml.: 25 ml.: 5 ml.) for 4 hrs. at about 25° C. under nitrogen. The solvents are removed under reduced pressure at 25°–40° C., and the residue is mixed with 25 ml. of water. The mixture is extracted several times with benzene, and the combined benzene layers are washed with water, dried over sodium sulfate, and finally concentrated under reduced pressure to the optically active Formula-IV acetal ketone having the same properties as reported above following section A. An alternate method of hydrolyzing the oxazolidine is on a silica gel-water column according to Example 13, thereafter eluting the released oxo compound and recovering same by conventional means.

EXAMPLE 15

Resolution of Tricyclic Lactone Aldehyde 16 (Formula VI: ~ is endo).

A. A solution of the endo Formula-VI lactone aldehyde (0.5 g.) of Example 4 and l-ephredrine (0.5 g.) in benzene (20 ml.) is concentrated under vacuum to a residue. The residue is treated with diethyl ether to yield crystals of an oxazolidine mixture. Recrystallization of the mixture from methanol yields an oxazolidine, m.p. 133.5–134.5. Thereafter, hydrolysis of the oxazolidine on a silica gel column following the procedure of Example 13 yields an optically active isomer corresponding to the mirror image of the Formula-VI lactone aldehyde, which is thereafter recovered by conventional means and is hereinafter identified as the "isomer of Example 15-A".

B. Following the procedure of Example 15-A, but replacing l-ephedrine with d-ephedrine in preparing the oxazolidine, the optically active isomer corresponding to the Formula-VI lactone aldehyde is obtained, hereinafter identified as the "isomer of Example 15-B".

Following the procedures of Example 15, the exo Formula-VI lactone aldehyde is resolved into its optically active isomers.

EXAMPLE 16

Optically Active Tricyclic Glycol (Formula VIII of chart a: W is 1-pentyl and ~ is endo); $PGE_2$, $PGF_{2\alpha}$, their ent-Compounds and their 15-Epimers.

Refer to chart C. Following the procedures of Examples 1 to 6, incclusive, but using the Formula-I endo-bicyclo[3.1.0]hex-2-ene-6-carboxaldehyde isomer of Example 13-A, there is obtained the Formula-VIII tricyclic glyhcol, wherein W is 1-pentyl and ~ is endo, as an optically active isomer. Following the procedures of Example 7, this isomer is transformed to the optically active Formula-IX and Formula-X compounds wherein W is 1-pentyl.

Likewise, using the Formula-I isomer of Example 13-C, there are obtained the enantiomorphic Formula-VIII, -IX, and -X compounds.

Each of the Formula-X isomers is transformed to the corresponding $PGE_2$, ent-$PGE_2$, and their 15-epimers, using methods known in the art by the steps shown in Chart C. Thus, $PGE_2$ is obtained from the optically active Formula-X diol prepared from the Formula-I aldehyde isomer of Example 13-A; ent-$PGE_2$ is obtained from the enantiomorphic Formula-X diol prepared from the Formula-I aldehyde isomer of Example 13-C.

Furthermore, again using the optically active Formula-VIII, -IX, and -X compounds prepared above, but following the steps of Chart E, using methods generally known in the art, there are obtained the corresponding $PGF_{2\alpha}$, ent-$PGF_{2\alpha}$, and their 15-epimers.

Following the procedures of Examples 1 to 6, inclusive, but substituting the optical isomers of the exo Formula-I aldehyde of Example 13 for the endo aldehyde, there are obtained the corresponding optically active exo Formula-VIII tricyclic glycols and Formula-IX bismesylates, which are converted to the isomeric Formula-X diols and thence to the corresponding $PGE_2$, ent-$PGE_2$, and their 15-epimers, $PGF_2$, $PFG_{2\alpha}$ and their 15-epimers.

EXAMPLE 17

$PGE_3$, ent-$PGE_3$ and their 15-Epimers, (Formula XXII of Chart D: ~ indicates the $\alpha$ or $\beta$ configuration).

Refer to Chart D. Following the procedures of Example 13, the endo Formula-I bicyclohexene aldehyde is resolved into its two optically active isomeric forms. Following the procedures of Example 11 and thereafter, each of the Formula-I isomers is transformed to the corresponding Formula-X diol in its $\alpha$ and $\beta$ configurations and thence to the corresponding $PGE_3$, ent-$PGE_3$, and their 15-epimers.

Following the procedures of Examples 14 and 15, the endo Formula-IV acetal ketone or the Formula-VI lactone aldehyde are resolved into their respective optically active isomeric forms. Following the procedures of Example 11 and thereafter, each of the Formula-IV or Formula-VI isomers is transformed to the corresponding Formula-X diol in its $\alpha$ and $\beta$ configurations and thence to the corresponding $PGE_3$, ent-$PGE_3$, and their 15-epimers.

Thus, $PGE_3$ is obtained from the optically active Formula-X diol prepared from the Formula-IV Acetal ketone of Example 14-A or the Formula-VI lactone aldehyde of Example 15-B; ent $PGE_3$ is obtained from the enantiomorphic Formula-X diol prepared from the Formula-IV acetal ketone of Example 14-C or the Formula-VI lactone aldehyde of Example 15-A.

Likewise, employing the exo forms of the Formula-I, -IV, and -VI compounds, these are resolved into their respective optically active isomeric forms and transformed to the corresponding Formula-X diol and thence to the corresponding $PGE_3$, ent-$PGE_3$, and their 15-epimers.

Likewise, following the procedures of Example 11 and thereafter, the optically active Formula-VIII glycol in its isomeric forms, wherein W is 1-pent-2-ynyl and ~ indicates attachment of the moiety to the cyclopropane ring in exo or endo configuration is subject successively to the following reactions:

a. replacement of the glycol hydrogens by an alkane-sulfonyl group, $R_9O_2S-$, wherein $R_9$ is alkyl of one to 5 carbon atoms, inclusive;

b. mixing with water at a temperature in the range of 0° to 60° C. to form a bicyclic lactone diol;

c. separation of the diols of $\alpha$ and $\beta$ configuration;

d. transformation to a bis(tetrahydropyranyl) ether;

e. reduction of the lactone oxo group to a hydroxy group;

f. Wittig alkylation with a compound of the formula $Hal-(CH_2)_4-COOH$ wherein Hal is bromo or chloro;

g. oxidation of the 9-hydroxy to oxo; and h. transformation of the two tetrahydropyranyloxy groups to hydroxy groups;

with the proviso that, before or after any of the steps a to h, the $-C \equiv C-$ moiety is reduced to cis $-CH=\lambda CH-$, thereby forming $PGE_3$, ent-$PGE_3$, or their 15-epimers.

EXAMPLE 18

$PGF_{3\alpha}$, ent-$PGF_{3\alpha}$, and their 15-epimers, (Formula XXVI of Chart F: ~ indicates the $\alpha$ or $\beta$ configuration).

Refer to Chart F. Following the procedures of Example 13, the endo Formula-I bicyclohexene aldehyde is resolved into its two optically active isomeric forms. Following the procedures of Example 12 and thereafter, each of the Formula-I isomers is transformed to the corresponding Formula-X diol in its $\alpha$ and $\beta$ configurations and thence to the corresponding $PGF_{3\alpha}$, ent-$PGF_{3\alpha}$, and their 15-epimers.

Following the procedures of Examples 14 and 15, the endo Formula-IV acetal ketone or the Formula-VI lactone aldehyde are resolved into their respective optically active isomeric forms. Following the procedures of Example 12 and thereafter, each of the Formula-IV or Formula-VI isomers is transformed to the corresponding Formula-X diol in its $\alpha$ and $\beta$ configuration and thence to the corresponding $PGF_3{}_\alpha$, ent-$PGF_3{}_\alpha$, and their 15-epimers.

Likewise, employing the exo forms of the Formula-I, -IV, and -VI compounds, these are resolved into their respective optically active isomeric forms and transformed to the corresponding Formula-X diol in its $\alpha$ and β configuration and thence to the corresponding PGF$_{3\alpha}$, ent-PGF$_{3\alpha}$ and their 15-epimers.

Likewise, following the procedures of Example 12 and thereafter, the optically active Formula-VIII glycol in its isomeric forms, wherein W is 1-pent-2-ynyl and ~ indicates attachment of the moiety to the cyclopropane ring in exo or endo configuration is subjected successively to the following reactions:

a. replacement of the glycol hydrogens by an alkanesulfonyl group, R$_9$O$_2$S—, wherein R$_9$ is alkyl of one to 5 carbon atoms, inclusive;

b. mixing with water at a temperature in the range of 0° to 60° C. to form a bicyclic lactone diol of S and R configuration;

c. separation of the diols of S and R configuration;

d. reduction of the lactone oxo group to a hydroxy group; and e. Wittig alkylation with a compound of the formula Hal—(CH$_2$)$_4$—COOH wherein Hal is bromo or chloro; with the proviso that, before or after any of the steps a to e, the —C≡C— moiety is reduced to cis —CH=CH—, thereby forming PGF$_{3\alpha}$, ent-PGF$_{3\alpha}$, or their 15-epimers.

EXAMPLE 19 dl-Tricyclic Lactone Epoxide (Formula XXXVIII: Y is n-pentyl, ~ indicates attachment to the cyclopropane ring in exo or endo configuration, and

indicates attachment of the epoxide oxygen to the side chain in α or β configuration).

Refer to Chart B. A mixture of the Formula-VII tricyclic lactone heptene of Example 5 (2.02 g.) and potassium bicarbonate (0.8 g.) in 12 ml. of dichloromethane is treated with peracetic acid (2 ml. of 40% in 8 ml. of dichloromethane) added dropwise over 10 min. After the starting material has been converted to the product as shown by TLC (about 45 hrs. at 25° C), the mixture is diluted with 30 ml. of dichloromethane and washed twice with 5% sodium bicarbonate containing sodium thiosulfate (0.5 g.). The dichloromethane solution is dried over anhydrous sodium sulfate and concentrated under reduced pressure to a residue of the title product, 2.18 g., NMR peaks at 0.6–3.3, 4.8 (broad) δ.

EXAMPLE 20 dl-Bicyclic Lactone Diformate (Formula XL: Y is n-pentyl and ~ is alpha and beta). Refer to Chart B.

Procedure A — A solution of the mixed Formula-VIII glycols (Formula XXXIX wherein M and E are hydrogen) of Example 6 (2.38 g.) in 40 ml. of 100% formic acid is left standing 5.5 hrs. at about 25° C. The mixture is then concentrated under reduced pressure to an oily residue. The residue is treated with a solution of phosphate buffer (pH 6.8) and about 10% sodium bicarbonate and extracted with dichloromethane. The dichloromethane solution is dried over sodium sulfate and concentrated under reduced pressure to a residue containing the title product, 2.66 g.

Procedure B — A solution of the Formula-XXXVIII epoxide of Example 19 (10.0 g.) in 80 ml. of a mixture of acetone-water-formic acid (70:30:2 by volume) is left standing 55 min. at about 25° C. The mixture is concentrated under reduced pressure to a residue. The residue is treated with 5% sodium bicarbonate, saturated with sodium chloride, and extracted with ethyl acetate. The ethyl acetate solution is dried over magnesium sulfate and concentrated under reduced pressure to a mixture of glycol XXXIX (M and E are hydrogen) and diol X, 11.7 g.

A solution of the above glycol-diol mixture in 350 ml. of 100% formic acid is left standing 2 hrs. at about 25° C. The mixture is then concentrated under reduced pressure and the residue taken up in dichloromethane. The dichloromethane solution is washed with 5% sodium bicarbonate, dried over sodium sulfate and concentrated to a residue containing the title product, 13.2 g.

Procedure C — A solution of the Formula-XXXVIII epoxide of Example 19 (2.18 g.) in 40 ml. of 100% formic acid (see for example Winstein et al., J. Am. Chem. Soc. 74, 1120 (1952)) is stirred under nitrogen for 2–3 hrs. at about 25° C., monitoring the reaction by TLC. The mixture is concentrated under reduced pressure to a residue. The residue is taken up in 50 ml. of dichloromethane and the solution washed with 5% sodium bicarbonate. The dichloromethane solution is dried over sodium sulfate and concentrated under reduced pressure to a residue containing the Formula-XL title product, 2.92 g.

EXAMPLE 21 dl-Bicyclic Lactone Diol (Formula X: W is 1-pentyl and ~ is alpha or beta).

Refer to Chart B. A solution containing the Formula-XL diformates of Example 20 (2.92 g.) in 10 ml. of methanol is stirred with potassium bicarbonate (0.2 g.) for 0.5 hr. The mixture is then filtered and the filtrate is diluted with 50 ml. of dichloromethane. The solution is washed with brine, dried over magnesium sulfate, and concentrated under reduced pressure to a residue. The residue is chromatographed on silica gel (810 g.) packed in acetone-dichloromethane (30:70), eluting with acetone-dichloromethane (30—45% acetone) and collecting 200 ml. fractions. Fractions shown by TLC to contain the desired products free of starting materials and impurities are combined, for example fractions 20—25 contain the X$_\beta$ title compound and fractions 26–35 contain the X$_\alpha$ title compound. Concentration of the respective fractions yields the title compounds: diol X$_\beta$, 0.66 g.; diol X$_\alpha$, 0.76 g.

EXAMPLE 22 dl-Tricyclic Lactone Monoformate (FIG. XXXIX: M and E are hydrogen or formyl, Y is 1-pentyl, and ~ indicates attachment to the cyclopropane ring in endo configuration, and to the side chain in alpha or beta configuration).

A solution of the mixed Formula-VIII glycols (Formula XXXIX wherein M and E are hydrogen) of Example 6 (2.38 g.) in 40 ml. of 100% formic acid is left standing 0.5 hr. at about 25° C. The mixture is then concentrated under reduced pressure. The residue is treated with a solution of phosphate buffer (pH 6.8) and about 10% sodium bicarbonate and extracted with dichloromethane. The dichloromethane solution is dried over sodium sulfate and concentrated under reduced pressure. The residue is separated by chromatography on silica gel, combining those fractions shown by TLC to contain the title compound. Concentration of those fractions yields the title compound. $R_f$=0.2 in ethyl acetate-Skellysolve B (40:60) on TLC plates.

EXAMPLE 23

$PGF_{2\alpha}$ and $15\beta$-$PGF_{2\alpha}$. Refer to Chart E.

A. Optically active tricyclic lactone acetal V — A mixture of the Formula-IV acetal ketone isomer of Example 14-A (12.0 g.) and potassium bicarbonate (6.1 g.) in 100 ml. of dichloromethane is treated with m-chloroperbenzoic acid (12.3 g. of 85%) in portions, with stirring and cooling to maintain the temperature below 30° C. After 2 hrs., 150 ml. of 5% sodium bicarbonate solution containing 9 g. of sodium thiosulfate is added. The dichloromethane layer is dried over anhydrous sodium sulfate and concentrated under reduced pressure. The residue is recrystallized from ethyl acetate as the Formula-V tricyclic lactone acetal wherein $R_1$ and $R_2$ taken together are —$CH_2$—$C(CH_3)_2$—$CH_2$— and ~ is endo; m.p. 127°–130° C., NMR peaks at 0.80, 1.29, 3.45, 3.72, 3.94 (doublet), and 4.89 (multiplet) δ; infrared absorption peaks at 1765, 1230, 1185, 1160, 1120, 1100, 1095, 1015, 1000, 980, 955, and 925 cm$^{-1}$; $[\alpha]_D^{25}$ +9° (methanol).

B. Optically active tricyclic lactone aldehyde VI — The acetal ketone of Example 23-A above (4.43 g.) is dissolved in 60 ml. of 88% formic acid and held at about 50° C. for 1 hr. The solution is cooled and diluted with 60 ml. of 1 N sodium hydroxide saturated with sodium chloride, and then extracted with several portions of dichloromethane. The dichloromethane extracts are washed with 20 ml. of 10% sodium carbonate, dried over anhydrous sodium sulfate, and concentrated under reduced pressure. The resulting oil is triturated with isopropyl ether and seeded to yield crystals of the corresponding Formula-VI tricyclic lactone aldehyde, m.p. 62.5–64° C., NMR peaks at 2.48 (doublet), 2.82 (doublet), 3.10 (multiplet), 5.12 (multiplet), and 9.84 (doublet); infrared absorption peaks at 1755, 1710, and 1695; $[\alpha]_D^{25}$ −30° (methanol).

C. Optically active tricyclic lactone heptene VII — Following the procedure of Example 5, the lactone aldehyde of Example 23-B above is transformed to the corresponding Formula-VII optically active lactone heptene; NMR peaks at 0.6–3.0, 4.5–5.2, and 5.7 δ; infrared absorption peak at at 1700 cm$^{-1}$.

D. Bicyclic lactone diol X — Following the procedures of Examples 19 to 21, the tricyclic lactone heptene of Example 23-C above is transformed to the corresponding optically active Formula-$X_\alpha$ and -$X_\beta$ lactone diols.

E. Title compounds — Following the methods known in the art, the above diols are transformed to the corresponding $PGF_{2\alpha}$ and $15\beta$-$PGF_{2\alpha}$ products.

Following the procedures of steps C, D, and E above, the optically active isomers of the Formula-VI aldehyde of Example 15 are transformed to $PGF_2$-type products. Thus, $PGF_{2\alpha}$ and $15\beta$-$PGF_{2\alpha}$ are obtained from the isomer of Example 15-B; ent-$PGF_{2\alpha}$ and ent-$15\beta$-$PGF_{2\alpha}$ are obtained from the isomer of Example 15-A.

What is claimed is:

1. A process for resolving a racemic mixture of an oxo compound of the formula

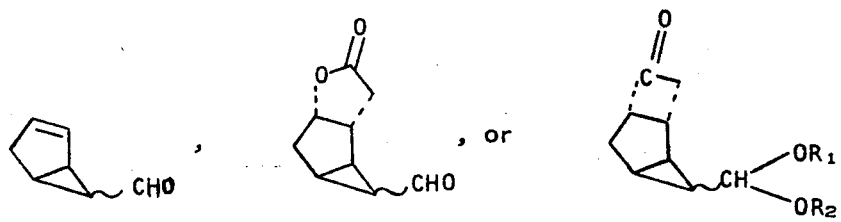

and of the mirror image thereof, wherein $R_1$ and $R_2$ are alkyl of one to 4 carbon atoms, inclusive, or, when taken together,

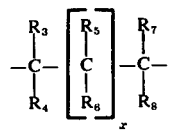

wherein $R_3$, $R_4$, $R_5$, $R_6$, and $R_8$ are hydrogen, alkyl of one to 4 carbon atoms, inclusive, or phenyl, with the proviso that not more than one of the R's is phenyl and the total number of carbon atoms is from 2 to 10, inclusive; $x$ is zero or one, and ~ indicates attachment of the moiety to the cyclopropane ring in exo or endo configuration, which comprises the steps of a. converting the oxo compound by reaction with an optically active ephedrine to a mixture of oxazolidine diastereomers, b. separating at least one oxazolidine diastereomer from said mixture, c. hydrolyzing said oxazolidine to free the optically active oxo compound, and d. recovering said optically active oxo compound.

2. A process of claim 1 wherein the oxo compound is an aldehyde of the formula

or of the mirror image thereof, wherein ~ indicates attachment of the moiety to the cyclopropane ring in exo or endo configuration.

3. A process of claim 1 wherein the oxo compound is an aldehyde of the formula

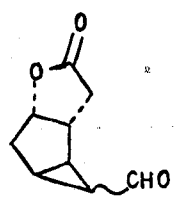

or the mirror image thereof, wherein ~ indicates attachment of the moiety to the cyclopropane ring in exo or endo configuration.

4. A process of claim 1 wherein the oxo compound is a ketone of the formula

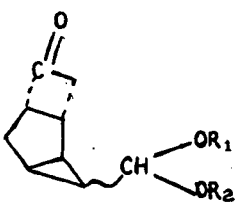

or of the mirror image thereof, wherein $R_1$, and $R_2$ are alkyl of one to 4 carbon atoms, inclusive, or, when taken together,

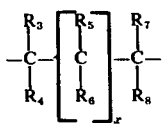

wherein $R_3$, $R_4$, $R_5$, $R_6$, and $R_8$ are hydrogen, alkyl of one to 4 carbon atoms, inclusive, or phenyl, with the proviso that not more than one of the R's is phenyl and the total number of carbon atoms is from 2 to 10, inclusive; $s$ is zero or one, and ~ indicates attachment of the moiety to the cyclopropane ring in exo or endo configuration.

5. A process of claim 4 wherein $R_1$ and $R_2$ taken together are $-CH_2-C(CH_3)_2-CH_2-$.

6. A process of claim 1 wherein the oxo compound is reacted with d-ephedrine.

7. A process of claim 1 wherein the oxo compound is reacted with l-ephedrine.

8. A process of claim 1 wherein the separating step is carried out by fractional crystallization from isopropyl ether.

9. A process of claim 1 wherein the separating step is carried out by fractional crystallization from methanol.

10. A process of claim 1 wherein the hydrolyzing step is carried out with water and an acid catalyst.

11. A process of claim 1 wherein the hydrolyzing step is carried out with water in the presence of silica gel.

* * * * *